US009950019B2

(12) United States Patent
Li et al.

(10) Patent No.: US 9,950,019 B2
(45) Date of Patent: Apr. 24, 2018

(54) COMPOSITIONS AND METHODS FOR THE PREVENTION AND TREATMENT OF BRAIN DISEASES AND CONDITIONS

(75) Inventors: Ming Li, New Territories (HK); Zhen Zhou, Shanghai (CN)

(73) Assignee: GENEREX PHARMACEUTICALS, INC., George Town (KY)

( * ) Notice: Subject to any disclaimer, the term of this patent is extended or adjusted under 35 U.S.C. 154(b) by 59 days.

(21) Appl. No.: 13/377,502

(22) PCT Filed: Jun. 11, 2010

(86) PCT No.: PCT/IB2010/001418
§ 371 (c)(1),
(2), (4) Date: Dec. 9, 2011

(87) PCT Pub. No.: WO2010/143063
PCT Pub. Date: Dec. 16, 2010

(65) Prior Publication Data
US 2012/0076878 A1    Mar. 29, 2012

Related U.S. Application Data

(60) Provisional application No. 61/186,709, filed on Jun. 12, 2009, provisional application No. 61/187,905, filed on Jun. 17, 2009.

(51) Int. Cl.
| A61K 31/56 | (2006.01) |
| A61K 36/00 | (2006.01) |
| A61K 31/565 | (2006.01) |
| A61K 31/7028 | (2006.01) |
| A61K 31/7032 | (2006.01) |
| A61K 31/7034 | (2006.01) |
| A61K 36/23 | (2006.01) |
| A61K 36/73 | (2006.01) |

(52) U.S. Cl.
CPC ............. *A61K 36/00* (2013.01); *A61K 31/56* (2013.01); *A61K 31/565* (2013.01); *A61K 31/7028* (2013.01); *A61K 31/7032* (2013.01); *A61K 31/7034* (2013.01); *A61K 36/23* (2013.01); *A61K 36/73* (2013.01)

(58) Field of Classification Search
None
See application file for complete search history.

(56) References Cited

U.S. PATENT DOCUMENTS

| 5,589,154 A * | 12/1996 | Anderson ............... 424/1.41 |
| 5,595,743 A | 1/1997 | Wu |
| 2001/0055630 A1 * | 12/2001 | Castillo et al. ........... 424/769 |
| 2002/0068098 A1 | 6/2002 | Babish et al. |
| 2003/0180395 A1 * | 9/2003 | Bueter ..................... 424/725 |
| 2004/0247698 A1 | 12/2004 | Valenzuela Cortes | |
| 2005/0064048 A1 | 3/2005 | Li et al. |
| 2008/0070826 A1 | 3/2008 | Selby, III |
| 2008/0260704 A1 | 10/2008 | Riordan et al. |
| 2009/0022827 A1 | 1/2009 | Li et al. |

FOREIGN PATENT DOCUMENTS

| CN | 1069629 | 3/1993 |
| CN | 1176814 | 3/1998 |
| CN | 1279970 | 1/2001 |
| CN | 1437973 | 8/2003 |
| CN | 1515311 | 7/2004 |
| CN | 1558769 | 12/2004 |
| CN | 1682788 | 10/2005 |
| CN | 1708313 | 12/2005 |
| CN | 101040901 | 9/2007 |
| CN | 101091751 | 12/2007 |
| CN | 101099770 | 1/2008 |
| CN | 101125171 | 2/2008 |
| CN | 101274012 | 10/2008 |
| CN | 101406537 | 4/2009 |
| JP | 2002-255804 | 9/2002 |
| JP | 2003-201229 | 7/2003 |
| JP | 2003-342190 | 12/2003 |
| JP | 2006-347967 | 12/2006 |
| JP | 2007-204447 | 8/2007 |
| JP | 2007-217352 | 8/2007 |
| JP | 2008-007417 | 1/2008 |
| JP | 2008-074801 | 4/2008 |
| KR | 100718602 | 5/2007 |
| KR | 20090020279 | 2/2009 |
| WO | WO-02/09720 | 2/2002 |

(Continued)

OTHER PUBLICATIONS

MayoClinic http://www.mayoclinic.com/health/alzheimers-disease/DS00161/METHOD=print&DSECTION=all.*
Vickers et a.: A Vaccine Vagainst Alzheimer's Disease.: Drugs Aging.: 2002.19 (7) pp. 487-494.*
H.B. MacPhillamy: Drugs From Plants; Plant Science Bulletin, Botanical Society of America, vol. 9, No. 2, Apr. 1963.*
Phillipson, J. New Drugs From Nature—It Could Be Yew; Phytotherapy Research 13 (1999) pp. 2-8.*
Raskin et al. Can an Apple a Day Keep the Doctor Away? Current Pharmaceutical Design, 2004, 10, 3419-3429.*
Revilla et al. Comparison of Several Procedures Used for the Extraction of Anthocynains From Red Grapes; J. Agric. Food Chem. 1998, 46, pp. 4592-4597.*

(Continued)

*Primary Examiner* — Terry A McKelvey
*Assistant Examiner* — Catheryne Chen
(74) *Attorney, Agent, or Firm* — Foley & Lardner LLP

(57) ABSTRACT

Disclosed herein are compounds, extracts, and active fractions of the plant *Geum japonicum* and methods for preventing or treating brain diseases or conditions, such as ischemic stroke, Alzheimer's disease, vascular dementia, mild cognitive impairment (MCI), chronic cerebral ischemia and Parkinson's disease. The compounds provided herein can be formulated into pharmaceutical compositions and medicaments that are useful in the disclosed methods. Also provided are the use of the compounds and extracts in preparing pharmaceutical formulations and medicaments.

10 Claims, 10 Drawing Sheets

(56) References Cited

FOREIGN PATENT DOCUMENTS

| WO | WO-02/078685 | 10/2002 |
| --- | --- | --- |
| WO | WO-03/043645 | 5/2003 |
| WO | WO 03/043645 A1 * | 5/2003 |
| WO | WO-2004/052381 | 6/2004 |
| WO | WO-2005/034958 | 4/2005 |
| WO | WO-2006/054370 | 5/2006 |
| WO | WO-2007/048352 | 5/2007 |
| WO | WO-2007/048353 | 5/2007 |
| WO | WO-2007/049088 | 5/2007 |
| WO | WO-2007/049089 | 5/2007 |
| WO | WO-2007/106049 | 9/2007 |
| WO | WO-2008/144706 | 11/2008 |
| WO | WO-2010/143058 | 12/2010 |
| WO | WO-2010/143059 | 12/2010 |
| WO | WO-2010/143061 | 12/2010 |
| WO | WO-2010/143062 | 12/2010 |
| WO | WO-2010/143063 | 12/2010 |
| WO | WO-2010/143065 | 12/2010 |

OTHER PUBLICATIONS

Smet et al. Herbal Remedies; The New England Journal of Medicine; Dec. 19, 2002, vol. 347, Issue 25, p. 2046, 11 pages.*
2015 https://www.nlm.nih.gov/medlineplus/degenerativenervediseases.html.*
2015 http://www.ninds.nih.gov/disorders/kuru/kuru.htm.*
Greenberg et al., From angiogenesis to neuropathology, 2005, nature, 438: 954-959.*
Desai et al., Evidence of angiogenic vessels in Alzheimer's disease, May 2009, J Neural Transm, 116: 587-597.*
Extended Search Report issued in European Application No. 10785823.5 dated Nov. 8, 2012 (12 pages).
Extended Search Report received in European Application No. 10785819.3 dated Nov. 8, 2012 (10 pages).
Extended Search Report received in European Application No. 10785820.1 dated Nov. 13, 2012 (7 pages).
Extended Search Report received in European Application No. 10785822.7 dated Nov. 8, 2012 (9 pages).
International Preliminary Report on Patentability issued for PCT/IB2010/001418 dated Nov. 22, 2012 (7 pages).
Kang, Soon Ah et al., "Antiinflammatory Activity of the Medicinal Plant Geum Japonicum," Nutritional Sciences, vol. 9, No. 2, (May 1, 2006), pp. 117-123.
Li, Ming et al., "Repair of Infarcted Myocardium by an Extract of Geum japonicum with Dual Effects on Angiogenesis and Myogenesis," Clinical Chemistry, vol. 52, No. 8, (Aug. 1, 2006), pp. 1460-1468.
Myeong-Sim, Ji et al., "Anticoagulant 1,2,3,4,6-pentagalloyl-beta-D-glucopyranos e isolated from geranium (Pelargonium inquinans Ait)," Archives of Pharmacal Research, vol. 28, No. 9, (Sep. 2005), pp. 1037-1041.
Non-Final Office Action received in U.S. Appl. No. 13/377,489 dated Nov. 21, 2012 (9 pages).
Samuels, Noah, "Herbal remedies and anticoagulant therapy," Thrombosis and Haemostasis, vol. 93, No. 1 (Jan. 1, 2005), pp. 3-7.
Somova, LO et al., "Cardiovascular, Antihyperlipidemic and Antioxidant Effects of Oleanolic and Ursolic Acids in Experimental Hypertension," Phytomedicine, vol. 10, No. 2-3, (Jan. 1, 2003), pp. 115-121.
Xie, Yi-Wu et al., "Role of Nitric Oxide in the Vasorelaxant and Hypotensive Effects of Extracts and Purified Tannins from Geum Japonicum," Journal of Ethnopharmacology, vol. 109, (2007), pp. 128-133.
Dong, H., et al., "Effects of Tannins from Geum japonicum on the Catalytic Activity of Thrombin and Factor Xa of Blood Coagulation Cascade," J. Nat. Prod., Oct. 1998, vol. 61, No. 11, pp. 1356-1360.
International Preliminary Report on Patentability received for PCT/IB2010/001410 dated Dec. 12, 2011.
International Preliminary Report on Patentability received for PCT/IB2010/001412 dated Dec. 12, 2011.
International Preliminary Report on Patentability received for PCT/IB2010/001415 dated Dec. 12, 2011.
International Preliminary Report on Patentability received for PCT/IB2010/001416 dated Dec. 12, 2011.
International Preliminary Report on Patentability received for PCT/IB2010/001418 dated Dec. 12, 2011.
International Preliminary Report on Patentability received for PCT/IB2010/001426 dated Dec. 12, 2011.
International Search Report received for PCT/IB2010/001410 dated Nov. 11, 2010.
International Search Report received for PCT/IB2010/001412 dated Nov. 11, 2010.
International Search Report received for PCT/IB2010/001415 dated Oct. 21, 2010.
International Search Report received for PCT/IB2010/001416 dated Nov. 11, 2010.
International Search Report received for PCT/IB2010/001418 dated Nov. 11, 2010.
International Search Report received for PCT/IB2010/001426 dated Nov. 11, 2010.
Li, J., "Studies on Bioactive Constituents with Myogenesis and Angiogenesis Activity from Geum Japonicum Thunb" Vax. Chinese F. Bolle, Chinese Doctoral Dissertation & Master's Thesis, Medicine and Health Sciences, Jan. 2007, 41 pages. (English abstract provided).
Liu, H., et al., "Fatty Acid Synthase Inhibitors from Geum Japonicum Thunb. var. Chinese," Chemistry & Biodiversity, Mar. 24, 2009, vol. 6, Issue 3, pp. 402-410.
Ming, D.S., et al. "Research Progress in Chemical Constituents and Biological Activities of Geum Species," Acta Pharmaceutica Sinica, 2000, vol. 35, No. 7, pp. 552-558.
Yoshiki, K., et al. "Antitumor agents, 129.[1] Tannins and Related Compounds as Selective Cytotoxic Agents," Journal of Natural Products, Aug. 1992, vol. 55, No. 8, pp. 1033-1043.
Zeng, F., et al., "The Anticoagulant Effects of Geum japonicum Extract and its Constituents," Phytotherapy Research, Mar. 1998, vol. 12, pp. 146-148.
Final Office Action on U.S. Appl. No. 13/377,489, dated Jul. 24, 2015.
Second Examination Report issued on Australian Application 2010258355, dated Aug. 5, 2015.
Final Office Action on U.S. Appl. No. 13/377,501, dated Jul. 9, 2015.
Final Office Action on U.S. Appl. No. 13/377,503, dated Jun. 29, 2015.
Office Action on Japanese Application 2012-514549, dated Feb. 25, 2015, English translation provided.
Office Action on Japanese Application 2012-514551, dated Feb. 23, 2015, English translation provided.
Office Action on Japanese Application 2012-514554, dated Feb. 25, 2015, English translation provide.
Examination Report No. 2 on Australian Application 2010258354, dated Apr. 1, 2015.
Examination Report on Australian Application 2010258356, dated Apr. 2, 2015.
Non-Final Office Action on U.S. Appl. No. 13/377,498, dated Apr. 13, 2015.
Final Office Action on U.S. Appl. No. 13/377,498 dated Jan. 20, 2016.
Non-Final Office Action on U.S. Appl. No. 13/377,501 dated Jan. 12, 2016.
Office Action issued on Japanese Application 2015-111092, dated Apr. 7, 2016 (English translation not available).
Zeng et al., "The Anticoagulant Effects of Geum japonicum Extract and its Constituents," Phytotherapy Research, vol. 12, 146-148, 1998.
Communication issued on EP Application 10785821.9, dated Mar. 2, 2016.
Examination Report issued on EP Application 10785823.5, dated Feb. 11, 2016.

(56) References Cited

OTHER PUBLICATIONS

Examination Report issued on EP Communication 10785822.7, dated Feb. 11, 2016.
Examination Report issued on European Application 10785820.1, dated Feb. 11, 2016.
Non-Final Office Action on U.S. Appl. No. 13/377,498 dated Feb. 8, 2017.
Office Action issued on Japanese application 2015-126332, dated Dec. 19, 2016.
Herrera et al, Functional Properties of Pentacylic Triterpenes Contained in "Orujo" Olive Oil, Current Nutrition & Food Science, 2006, pp. 45-49.
Kang et al., Anti-inflammatory Activity of the Medicinal Plant Geum Japonicum, Nutritional Sciences 9(2), May 2006, pp. 117-123.
Rodriguez-Rodriguez et al., "Triterpenic Compounds from "orujo" Olive Oil Elicite Vasorelation in Aorta from Spontaneously Hypertensive Rats," Journal of Agricultural and Food Chemistry, 2006, pp. 2096-2102.
Office Action issued on Japanese Application 2015-126506, dated May 23, 2016, English Translation.
Final Office Action on U.S. Appl. No. 13/377,501 dated Aug. 19, 2016.
Dubey et al., "Individuals at Risk of Coronary Heart Disease (CHD), its Prevention and Management by an Indigenous Compound," Ancient Science of Life, vol. No. XX (1&2), Jul.-Oct. 2000, p. 48-57.
Examination Report issued on European Application 10785818.5, dated Dec. 2, 2016.
Examination Report issued on European Application 10785819.3, dated Nov. 28, 2016.
Gnanapragasam et al., "Protective effect of Centella asiaticaon antioxidant tissue defense system against Adriamycin inducted cardiomyopathy in rats," Life Sciences 76, 2004, pp. 585-597.
Notice of Allowance on U.S. Appl. No. 13/377,501 dated Dec. 20, 2016.
Office Action issued on Japanese Application 2015-126506, dated Nov. 30, 2016.
Non-Final Office Action on U.S. Appl. No. 13/377,503 dated Jul. 14, 2016.
Office Action issued on Japanese Application 2012-514549, dated Jun. 16, 2016, English translation only.
Bhattachrya, Salil K. et al., "Effect of Bioactive Tannoid Principles of Emblica Officinalis on Ischemia-Reperfusion-Induced Oxidative Stress in Rat Heart," Phytomedicine, vol. 9, No. 2, Jan. 1, 2002, pp. 171-174.
Fogo, A.S et al., "Tormentic acid reduces vascular smooth muscle cell proliferation and survival," European Journal of Pharmacology, vol. 615, No. 1-3, Aug. 1, 2009, pp. 50-54.
Search Report issued in European Application No. 10785821.9 dated Feb. 15, 2013 (10 pages).
Search Report received in European Application No. 10785818.5 dated Feb. 19, 2013 (11 pages).
Euficreview, Web publication date: Nov. 1998 [Examiner retrieved from the internet on: Mar. 25, 2013], Retrieved from URL: http://www.eufic.org/article/en/expid/review-diet-lifestyle-life-expectancy/ (6 pages).
Non-Final Office Action issued for U.S. Appl. No. 13/377,501 dated Mar. 28, 2013 (17 pages).
Final Office Action issued in U.S. Appl. No. 13/377,489 dated May 22, 2013 (16 pages).
NDIC, "Diagnosis of Diabetes", Internet Archive Date: Feb. 28, 2005 [Retrieved from internet on: May 18, 2013 by USPTO Examiner]. Retrieved from the Internet: <URL: http://web.archive.org/web/20050228073517/http://diabetes.niddk.nih.gov/dm/pubs/diagnosis/> (7 pages).
Yoshida, et al., "Tannins of Rosaceous Medicinal Plants. Part 2. Gamins A, B, and C, New Dimeric Ellagitannins from Geum japonicum", J. Chem. Soc. Perkin Trans. I, (1985), pp. 315-321.

Adams, K.F. et. al.,"Clinical benefits of low serum digoxin concentrations in heart failure," Jnl of Am College of Cardiology, (2002), vol. 39, No. 6, pp. 946-953.
Anderson, Koren J. et al., "Walnut Polyphenolics Inhibit in Vitro Human Plasma and LDL Oxication 1,2," Jnl of Nutrition, (2001), 131(11), pp. 2837-2842.
Bonfill, M. et al., "Identification of triterpenoid compounds of Centella asiatica by thin-layer chromatography and mass spectrometry," Biomedical Chromatography, (2005), 20(2), pp. 151-153.
Brinkhaus, B. et al., "Chemical, pharmacological and clinical profile of the East Asian medical plan Centella aslatica," Phytomedicine, (2000), vol. 7(5), pp. 427-448.
Definitions of "Ischemic Heart Disease" and "Coronary Heart Disease" from Hyperdictionary, retreived on Sep. 11, 2013 from http://hyperdictionary.com.
Fukuda, Toshiyuki et al., "Antioxidative polyphenols from walnuts (Juglans regia L.)," Phytochemistry, (2003), 63(7), pp. 795-801.
Lapornik, Brigita et al., "Comparison of extracts prepared from plant by-products using different solvents and extraction time," (2005), Jnl Food Engineering, 71(2), pp. 214-222.
Larrosa, Mar et al., "Ellagitannins, ellagic acid and vascular health," Molecular Aspects of Medicine, (2010), 31(6), pp. 513-539.
Meredith, Peter A. et al., "From Hypertension to Heart Failure—Are there better primary prevention strategies?," Jnl of Renin-Angiotension-Aldosterone System, (Jun. 2006), vol. 7, No. 2, pp. 64-73.
Non-Final Office Action issued in U.S. Appl. No. 13/377,483 dated Aug. 22, 2013 (27 pages).
Non-Final Office Action issued in U.S. Appl. No. 13/377,503 dated Aug. 30, 2013 (28 pages).
Pragada, R.R. et al., "Carioprotective activity of *Hydrocotyle asiatica* L. in ischemia-reperfusion induced myocardial infarction in rats," Jnl of Ethnopharmacology, (2004), 93, pp. 105-108.
Turkmen, Nihal et al., "Effects of extraction solvents on concentration and antioxidant activity of black and black mate tea polyphenols determined by ferrous tartrate and Folin-Ciocalteu methods," (2006), Food Chemistry, 99(4), pp. 835-841.
Wojtczak, Dr. Andrzej, "Glossary of Medical Education Terms: 'Prevention'," (Feb. 2002), 5 pages.
Yoshida, Takashi et al., "Dimeric ellagitannins, laevigatins E, F and G from Rosa Laevigata," Phytochemistry, (1989), vol. 28, No. 9, pp. 2451-2454.
Final Office Action received in U.S. Appl. No. 13/377,501 dated Sep. 20, 2013 (12 pages).
Final Office Action received in U.S. Appl. No. 13/377,483 dated Mar. 28, 2014 (24 pages).
Final Office Action received in U.S. Appl. No. 13/377,503 dated Apr. 2, 2014 (18 pages).
Bhattacharya, Salil K. et al., "Effect of bioactive tannoid principles of Emblica officinalis on ischemia-reperfusion-induced oxidative stress in rat heart," Phytomedicine, (2002), vol. 9, pp. 171-174.
Dong-Sheng, Ming et al., "Research Progress in Chemical Constituents and Biological Activities of Geum Species," Acta Pharma, (2000), vol. 35, No. 7, pp. 552-558.
Office action received in Japanese Patent Application No. 2012-514548 dated Jun. 16, 2014, 7 pages, with English translation.
Office Action received in Japanese Patent Application No. 2012-514549 dated Jul. 2, 2014, 5 pages with English translation.
Office Action received in Japanese Patent Application No. 2012-514550 dated May 21, 2014, 6 pages with English translation.
Office Action received in Japanese Patent Application No. 2012-514551 dated Jun. 30, 2014, 9 pages with English translation.
Office Action received in Japanese Patent Application No. 2012-514552 dated May 26, 2014, 6 pages, with English translation.
Office Action received in Japanese Patent Application No. 2012-514554 dated May 28, 2014, 8 pages, with English Translation.
Patent Examination Report No. 1 received in Australian Patent Application No. 2010258351 dated Jul. 31, 2014, 4 pages.
Patent Examination Report No. 1 received in Australian Patent Application No. 2010258352 dated Jul. 7, 2014, 4 pages.
Patent Examination Report No. 1 received in Australian Patent Application No. 2010258354 dated Jul. 11, 2014, 3 pages.
Patent Examination Report No. 1 received in Australian Patent Application No. 2010258355 dated Jul. 31, 2014, 3 pages.

(56) References Cited

OTHER PUBLICATIONS

Examination Report No. 1 received in Australian Patent Application No. 2010258358 dated Oct. 15, 2014, 5 pages.
Ansel, Howard C. et al., Seventh Edition, Pharmaceutical Dosage Forms and Drug Delivery Systems, "Chapter 2: New Drug Development and Approval Process," (1999), 6 pages.
Non-Final Office Action received in U.S. Appl. No. 13/377,501 dated Jan. 2, 2015, 17 pages.
Non-Final Office Action received in U.S. Appl. No. 13/377,503 dated Jan. 6, 2015, 28 pages.
Non-Final Office Action received in U.S. Appl. No. 13/377,489 dated Jan. 5, 2015, 21 pages.
Examination Report issued on Australian Application 2016202674, dated Dec. 12, 2017.

* cited by examiner

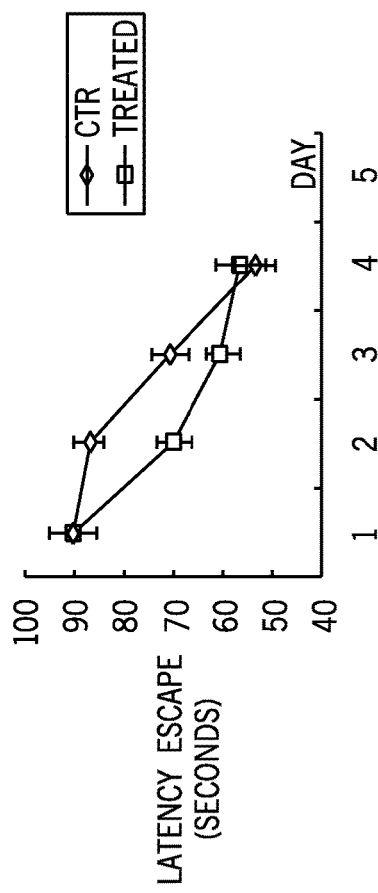
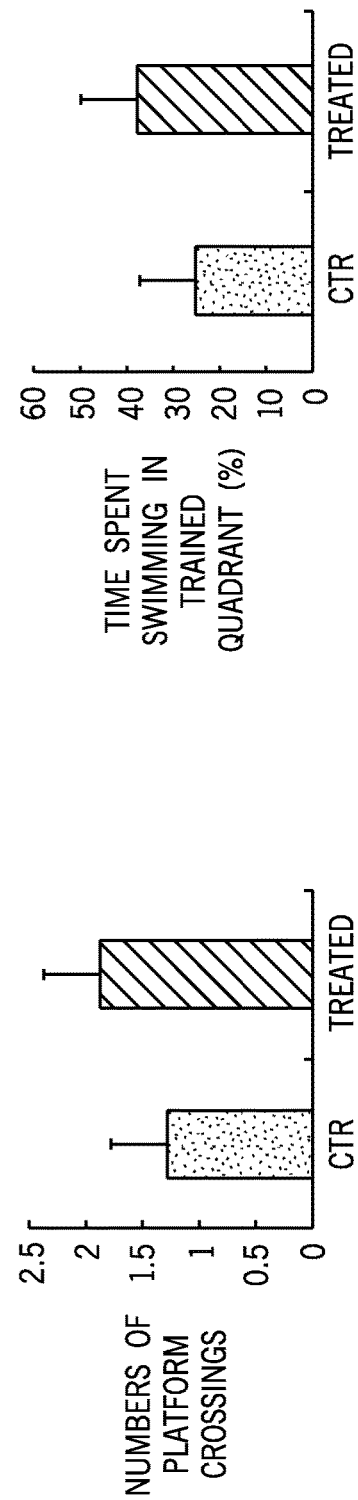
FIG. 10A
FIG. 10B
FIG. 10C

COMPOSITIONS AND METHODS FOR THE PREVENTION AND TREATMENT OF BRAIN DISEASES AND CONDITIONS

CROSS-REFERENCE TO RELATED APPLICATIONS

The present application is the U.S. National Stage Application of PCT International Application No. PCT/IB2010/001418, filed Jun. 11, 2010, which claims priority to U.S. Provisional Application No. 61/186,709, filed Jun. 12, 2009, and U.S. Provisional Application No. 61/187,905, filed Jun. 17, 2009, the entire contents of which are hereby incorporated by reference in their entirety.

SUMMARY

This invention is directed to a pharmaceutical composition and a method of treating stroke, Alzheimer's disease, vascular dementia, chronic cerebral ischemia and Parkinson's disease in mammals. In some embodiments, the present invention relates to a pharmaceutical composition and method for substantially improving cerebral blood flow to an ischemic brain by growing new collateral vessels and by inducing neuronal regeneration. Both the improved microenvironment with restored blood supply and the enhanced neurogenesis potency may stimulate regeneration of neurons and replace the dead neuronal cells. As such, the present compositions and methods are useful for the treatment of stroke, Alzheimer's disease, vascular dementia, chronic cerebral ischemia and Parkinson's disease in humans and may restore some of the lost functions due to these neuronal degenerative diseases.

In one aspect, the present invention relates to an organic extract of Geum japonicum (OEGJ) for the treatment of stroke, Alzheimer's disease, vascular dementia, chronic cerebral ischemia and Parkinson's disease. The present inventors have discovered that OEGJ can exert multiple functions: (1) significantly promote differentiation of vessel endothelial cells forming tube like structures and stimulate physical reconstitution of the insufficient blood supply to the brain that will substantially rectify the brain ischemia and improve the microenvironment of neurons; (2) enhance neural cell survival that will protect neurons at risk from ischemia and stress; (3) induce neurogenic differentiation of stem cells in vitro and neuronal regeneration in vivo for the replacement of damaged or lost neurons.

Stroke, Alzheimer's disease, vascular dementia, chronic cerebral ischemia and Parkinson's disease are severe cerebral-vascular associated and age-related degenerative diseases. The effective treatment of these diseases addressing their root pathology should include two goals: (i) reconstituting the blood flow to the ischemic brain by substantial growth of new collateral vessels in the brain and, (ii) regeneration of neurons by replacing the lost neuronal cells. Therefore, in accordance with one embodiment, OEGJ can effectively treat stroke, Alzheimer's disease, vascular dementia, chronic cerebral ischemia and Parkinson's disease and help the affected brain regain some of its lost function, e.g., speech, physical activities, memory, and cognitive and learning abilities. In another embodiment, OEGJ can enhance the survival of neurons at risk or under stress. In another embodiment, OEGJ can slow down the progression of stroke, Alzheimer's disease, vascular dementia, chronic cerebral ischemia and Parkinson's disease. In another embodiment, OEGJ can prevent stroke, Alzheimer's disease, vascular dementia, chronic cerebral ischemia and Parkinson's disease in high-risk populations.

In one aspect, the present disclosure provides a method for preventing or treating a degenerative neuronal disease or condition in a mammalian subject, the method comprising: administering to a subject in need thereof an effective amount of an organic extract of Geum japonicum. In one embodiment, the degenerative neuronal disease or condition is selected from the group consisting of: ischemic stroke, Alzheimer's disease, vascular dementia, mild cognitive impairment (MCI), chronic cerebral ischemia and Parkinson's disease. In one embodiment, the administration enhances brain blood perfusion or neuronal regeneration in a subject having an ischemic stroke compared to a control subject not administered the extract of Geum japonicum. In one embodiment, the extract of Geum japonicum induces angiogenesis of an ischemic brain thereby enhancing blood perfusion. In one embodiment, the extract of Geum japonicum stimulates neuronal regeneration. In one embodiment, the extract of Geum japonicum reduces the size of the brain ischemic infarcted area compared to a subject not treated with an extract of Geum japonicum.

In one embodiment, the extract of Geum japonicum is administered in an amount ranging from about 0.001 mg to about 1000 mg of the extract per kilogram of subject body weight per day. In one embodiment, the extract of Geum japonicum is administered in a dosage unit form including a pharmaceutically acceptable carrier. In one embodiment, the extract of Geum japonicum is administered orally. In one embodiment, the extract of Geum japonicum is administered by subcutaneous injection, intramuscular injection, or intravenous infusion.

In one embodiment, the extract is a lower alkyl alcohol extract of Geum japonicum. In one embodiment, the lower alkyl alcohol has 1-6 carbon atoms. In one embodiment, the lower alkyl alcohol is ethanol. In one embodiment, the subject is a human.

In one aspect, the present disclosure provides a pharmaceutical composition for treating a degenerative neuronal disease or condition in a mammalian subject comprising an effective amount of an organic extract of Geum japonicum and a pharmaceutically acceptable carrier.

BRIEF DESCRIPTION OF THE FIGURES

FIG. 10. Water maze assessment of spatial learning and memory capacity in APP mice. Animals were trained 3 times a day for 4 days. On the fifth day, the mice were subjected to a probe trial. (Ctr) Denotes vehicle-treated mice. Treated, OEGJ-treated. (a) The vehicle-treated animals (Ctr) exhibited a significantly longer latency in finding the hidden platform compared to that in OEGJ-treated mice (treated) ($P<0.01$). The prolonged escape latency was significantly reduced by oral administration of OEGJ (480 mg/kg/day for one month) ($P<0.01$); (b) the probe trial was carried out on day 5 immediately after the last training trial. There were significant group effects on the time spent in the target quadrant where the platform had been located during the training trials. The number of platform crossings was significantly higher in OEGJ-treated mice (Treated) than that in vehicle-treated (Ctr) ($P<0.01$); and (c) the OEGJ-treated mice (Treated) spent approximately 40% of their swimming time in the trained platform quadrant. In comparison, the mice in the vehicle treated group (Ctr) spent about 26% of their swimming time in the trained platform quadrant, significantly shorter than that in OEGJ-treated mice ($P<0.01$).

DETAILED DESCRIPTION

Figure 1:
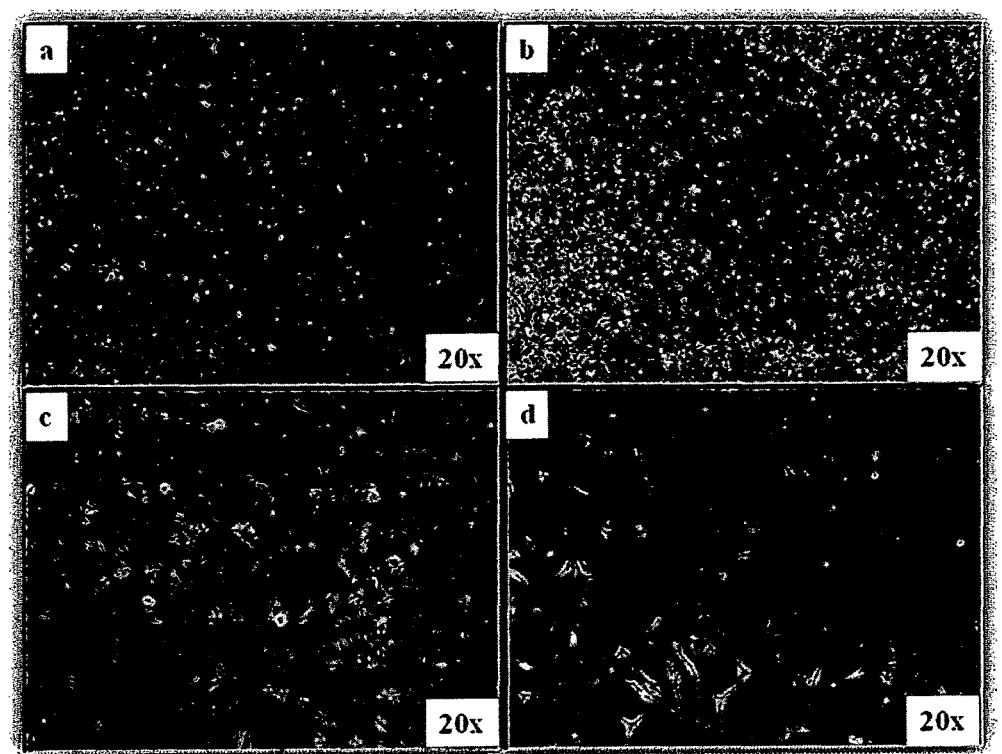
FIG. 1. OEGJ induced differentiation of human umbilical vein endothelial cells (HUVEC). (a) The vehicle-treated cells showing no differentiation; (b) OEGJ (50 µg/ml) treated cells showing proliferation promoting effect; (c) OEGJ (100 µg/ml) treated cells showing elongated phenotype. Some of the cells formed tube-like structures; and (d) OEGJ (200 µg/ml) treated cells. All cells were well differentiated into elongated and tube-like structures.

This disclosure relates generally to bioactive substances from *Geum japonicum*. In particular, the present disclosure relates to pharmaceutical preparations and dietary supplements to prevent or treat degenerative neuronal conditions, including stroke, Alzheimer's disease, vascular dementia, mild cognitive impairment, chronic cerebral ischemia and Parkinson's disease. The compounds provided herein can be formulated into pharmaceutical compositions and medicaments that are useful in the disclosed methods. Also provided are the use of the compounds and extracts in preparing pharmaceutical formulations and medicaments.

It is to be appreciated that certain aspects, modes, embodiments, variations and features of the invention are described below in various levels of detail in order to provide a substantial understanding of the present invention. The following terms are used throughout as described below, unless context clearly indicates otherwise.

As used herein, the "administration" of an agent or drug to a subject or subject includes any route of introducing or delivering to a subject a compound to perform its intended function. Administration can be carried out by any suitable route, including orally, intranasally, parenterally (intravenously, intramuscularly, intraperitoneally, or subcutaneously), rectally, or topically. Administration includes self-administration and the administration by another. It is also to be appreciated that the various modes of treatment or prevention of medical conditions as described are intended to mean "substantial", which includes total but also less than total treatment or prevention, and wherein some biologically or medically relevant result is achieved.

As used herein, the term "effective amount" or "pharmaceutically effective amount" or "therapeutically effective amount" of a composition, is a quantity sufficient to achieve a desired therapeutic and/or prophylactic effect, e.g., an amount which results in the prevention of, or a decrease in, the symptoms associated with a disease that is being treated. The amount of a composition of the invention administered to the subject will depend on the type and severity of the disease and on the characteristics of the individual, such as general health, age, sex, body weight and tolerance to drugs. It will also depend on the degree, severity and type of disease. The skilled artisan will be able to determine appropriate dosages depending on these and other factors. The compositions of the present invention can also be administered in combination with one or more additional therapeutic compounds.

The abbreviation "OEGJ" used in the invention, without specific indication, means an extract of the plant *Geum japonicum* by an organic solvent described below.

As used herein, the term "disease" or "medical condition" are used interchangeably and includes, but is not limited to, any condition or disease manifested as one or more physical and/or psychological symptoms for which treatment and/or prevention is desirable, and includes previously and newly identified diseases and other disorders. For example, a medical condition may be stroke, dementia, Alzheimer's disease, Parkinson's disease, or chronic cerebral ischemia.

As used herein, the term "subject" refers to a mammal, such as a human, but can also be an animal, e.g., domestic animals (e.g., dogs, cats and the like), farm animals (e.g., cows, sheep, pigs, horses and the like) and laboratory animals (e.g., monkey, rats, mice, rabbits, guinea pigs and the like).

As used herein, the terms "treating" or "treatment" or "alleviation" refers to both therapeutic treatment and prophylactic or preventative measures, wherein the object is to prevent or slow down (lessen) the targeted pathologic condition or disorder. A subject is successfully "treated" for a disorder if, after receiving a therapeutic agent according to the methods of the present invention, the subject shows observable and/or measurable reduction in or absence of one or more signs and symptoms of a particular disease or condition.

As used herein, "prevention" or "preventing" of a disorder or condition refers to a compound that, in a statistical sample, reduces the occurrence of the disorder or condition in the treated sample relative to an untreated control sample, or delays the onset or reduces the severity of one or more symptoms of the disorder or condition relative to the untreated control sample.

Compositions of the Invention

The present invention provides methods of treating or preventing a variety of diseases or medical conditions with extracts and compounds, and derivatives of such compounds from a variety of plants including *Geum japonicum*; Xian he cao (also known as *Agrimonia pilosa* Ledeb. (Rosaceae); and *Thymus mongolicus Ronn* (Lamiaceae), Herba Thymi or Mongolian Thyme Herb). In some embodiments, the compound is a whole plant, an extract, e.g., an organic extract, of *Geum japonicum*, Xian he cao, *Agrimonia pilosa* Ledeb. (Rosaceae); *Thymus mongolicus Ronn* (Lamiaceae). In a particular embodiment, the compound is a methanol/ethanol extract of *Geum japonicum* or an active fraction thereof. In some embodiments, the compound is a fraction of an extract of *Geum japonicum*.

The present invention provides methods of treating or preventing a variety of diseases or medical conditions with agents and/or extracts and compounds, and derivatives of such compounds from a variety of plants including *Geum japonicum*. In some embodiments, the agent is an extract, e.g., an organic extract, of *Geum japonicum*. In a particular embodiment, the agent is a methanol/ethanol extract of *Geum japonicum* or an active fraction thereof.

A method for preparing an organic extract from *Geum japonicum* is provided. This method comprises the step of (a) extracting the dried whole plant of *Geum japonicum* Thunb with alcohol selected from the group consisting of C1-C4 alcohols. This step may be repeated 3-6 times, typically 5 times, at room temperature. Before performing step (a) the plant material may be powdered or cut into small pieces. The C1-C4 alcohols include methanol, ethanol, n-propanol, iso-propanol, n-butanol, iso-butanol, and ter-butanol. Typically, alcohol is added in 1-10 times by weight of the amount of the dried *Geum japonicum* to be extracted.

The methods may further comprise the step of (b) drying the extract obtained from the step of (a) into a dried powder; and (c) successively extracting the powder obtained from the step of (b) with C6 alkane, EtOAc and an alcohol selected from the group consisting of C1-C4 alcohols. The C6 alkane includes cyclic and non-cyclic alkane having 6 carbon atoms, including, for example, cyclohexane, n-hexane, and neo-hexane, etc. The C1-C4 alcohols include methanol, ethanol, n-propanol, iso-propanol, n-butanol, iso-butanol, and ter-butanol. The amount of organic solvent to be used is typically 1-10 times by weight of the amount of the powders or small pieces to be further extracted.

The method as recited above may also include filtering the extract to remove any insoluble powders therein. A drying step may be completed under reduced pressure at a temperature higher than room temperature, for example, at 50° C. or by electrospray.

To purify the OEGJ, the method may further comprise the steps of applying the powder to a chromatographic column; and eluting the column with an aqueous solution with increasing concentration of an alcohol selected from the group consisting of C1-C4 alcohols. For example, a Sephadex or reverse phase column may be used. The alcohol used may be any one selected from the group consisting of methanol, ethanol, n-propanol, iso-propanol, n-butanol, iso-butanol, and ter-butanol.

By NMR analysis, it is found that the OEGJ typically contains mainly tannins, including gemin A, B, C, D, E and F and triterpenes, including 2-hydroxyoleanolic acid, 2-hydroxylursolic acid, 2,19-dihydroxy-ursolic acid, 2-$\alpha$,19-$\alpha$-dihydroxy-3-oxo-12-ursen-28-oic acid, ursolic acid, epimolic acid, maslinic acid, euscaphic acid, tormentic acid, 28-$\beta$-D-glucoside of tormentic acid.

In one embodiment, the extracts, fractions, and compounds of the invention are obtained by extraction, using water and/or of an organic solvent, from crude plant material comprises the following stages:
1. Extraction by addition to the plant material, of water and/or of organic solvent(s), by subjecting the whole to a treatment such as maceration/lixiviation, ultrasonics or microwaves;
2. Delipidation before or after the extraction stage using a solvent of petroleum ether, hexane or chloroform type;
3. Optionally, additional extraction of the extract recovered by an organic solvent of ethyl acetate or ethyl ether type,
4. Optionally, concentration of the crude extract obtained, and, if desired, its lyophilization.

According to one aspect, considering the enrichment that it allows to be attained, the crude extract may be subjected to a purification stage by chromatography. In one embodiment, centrifugal partition chromatography (CPC) is used. This technique is in particular described by A. P. FOUCAULT, Ed., Centrifugal Partition Chromatography, Chromatographic Science Series, Marcel Dekker Inc., 1995, 68, or W. D. CONWAY, Ed., Countercurrent Chromatography apparatus theory and applications, VCH Publishers Inc., 1990. CPC is based on the partition of the solutes between two non-miscible liquid phases prepared by the mixture of two or more solvents or solutions. One of the two phases is kept stationary by a centrifugal force. The solvents, their proportions and the flow rate chosen closely depend both on the stability of the stationary phase within the CPC column and the actual pressure.

A person skilled in the art will therefore choose the most appropriate solvent or solvents depending on the nature of the purified extract desired. These different extracts, namely crude or enriched also fall within the scope of the invention. The implementation of additional separation stages allows isolation of these extracts enriched with one or more compounds. These separations can be carried out on fractions enriched from a crude extract or on the crude extract itself by using mixtures of appropriate solvents according to the proportions that are suitable for the sought separation.

Methods and Compositions for the Prevention or Treatment of Stroke

Stroke occurs when a blood vessel that brings oxygen and nutrients to the brain is either clogged by a blood clot or some other mass (ischemic stroke) or bursts (hemorrhagic stroke). When an ischemic stroke occurs, the blood supply to the brain is interrupted, and thus brain cells are deprived of the glucose and oxygen they need to survive and function. As a result, brain cells in the affected region cannot work properly which means the part of the body they control cannot work either. The damage that results depends on how long brain cells are deprived of blood. If brain cells are deprived longer, brain cells die and some functions may be irrevocably lost. The devastating effects of a severe stroke are often permanent because dead brain cells cannot be regenerated naturally.

Ischemic stroke is the most common type of stroke which accounts for about 85% of all strokes. It occurs when a blood clot (thrombus) forms and blocks blood flow in an artery bringing blood to part of the brain. Ischemic stroke is further divided into thrombotic stroke and embolic stroke. When the blood clot forms within an artery of the brain, it is called a thrombotic stroke. These often occur at night or first thing in the morning. Another distinguishing feature is that they are often preceded by a transient ischemic attack (TIA) or "warning stroke". TIAs have the same symptoms of stroke but they resolve within an hour while stroke symptoms last much longer. An embolic stroke refers to the blockage of an artery by an embolus, a traveling particle or debris in the arterial blood stream originating from elsewhere. Emboli most commonly arise from the heart, especially in atrial fibrillation, but may originate from elsewhere in the arterial tree.

Specific treatment of stroke may include drugs to break up blood clots (thrombolytic drugs), drugs to make blood less likely to clot (antiplatelet drugs and anticoagulants), and surgery. In many primary stroke centers, the drug tissue plasminogen activator (tPA) is used to dissolve the clot and unblock the artery. However, the use of tPA in acute stroke is controversial. Because tPA can cause bleeding in the brain and elsewhere, it should not be given to people with a tendency to bleed. To be effective and safe, tPA must be started within 3 hours of the beginning of an ischemic stroke. After 3 hours, most of the damage to the brain cannot be reversed, and the risk of bleeding outweighs the possible benefit of the drug. However, pinpointing when the stroke began may be difficult. Thus, tPA can be used in only a few people who have had a stroke. If a thrombolytic drug cannot be used, most people are given aspirin (an antiplatelet drug) that can reduce the risk of another ischemic stroke. Antiplatelet drugs make platelets less likely to clump and form clots, a common cause of ischemic stroke. However, antiplatelet drugs increase the risk of bleeding.

After a stroke, neurons in the brain can be divided into three groups: dead neurons, surviving neurons, and quiescent neurons that are slowly shrinking and deteriorating over an extended period of time. It is well known that neurons cannot regenerate, therefore, it is imperative to rescue the quiescent neurons before permanent tissue damage or death occurs. The question arises as to what is the pathological cause of neuronal deterioration and death. There is increasing evidence that the cause of the decline in neuronal activity in stroke patients may be the result of decreasing cerebral blood flow that is necessary for continued function and survival of individual neurons. Interestingly, it has been observed that when the large arteries that supply the brain are blocked, some people have no symptoms or have only a small stroke while others have a massive ischemic stroke. One possible explanation lies in the collateral arteries between other arteries, providing extra connections. Some people are born with more collateral arteries that may protect them from a stroke when one artery is blocked. Others are born with fewer collateral arteries so that when one artery is blocked there may not be enough blood supply to the affected area. Hence, remedies that can promote growth of new collateral arteries and increase blood perfusion in the brain are expected to provide effective treatment for ischemic stroke.

The present inventors discovered that OEGJ was not only able to restore the blood perfusion to the ischemic brain, but also enhanced the survival potential of stressed neurons. The compositions also induced neuronal differentiation of mesenchymal stem cells and neuronal regeneration. In some embodiments, one or two month's treatment with OEGJ induced significant therapeutic effects in animal models of ischemic stroke and human stroke patients. Therefore, OEGJ is useful in methods to effectively treat and prevent ischemic stroke, and is useful in post-stroke rehabilitation.

In one aspect, there is provided a pharmaceutical composition for treating ischemic stroke which comprises a collection of natural compounds derived from the OEGJ. The OEGJ has shown potent beneficial therapeutic effects in treating ischemic stroke by promoting blood perfusion of the ischemic brain by promoting the growth of new collateral vessels, protecting against neuronal cell apoptosis, rescuing the neural cells at risk and promoting regeneration of neurons.

Figure 2:
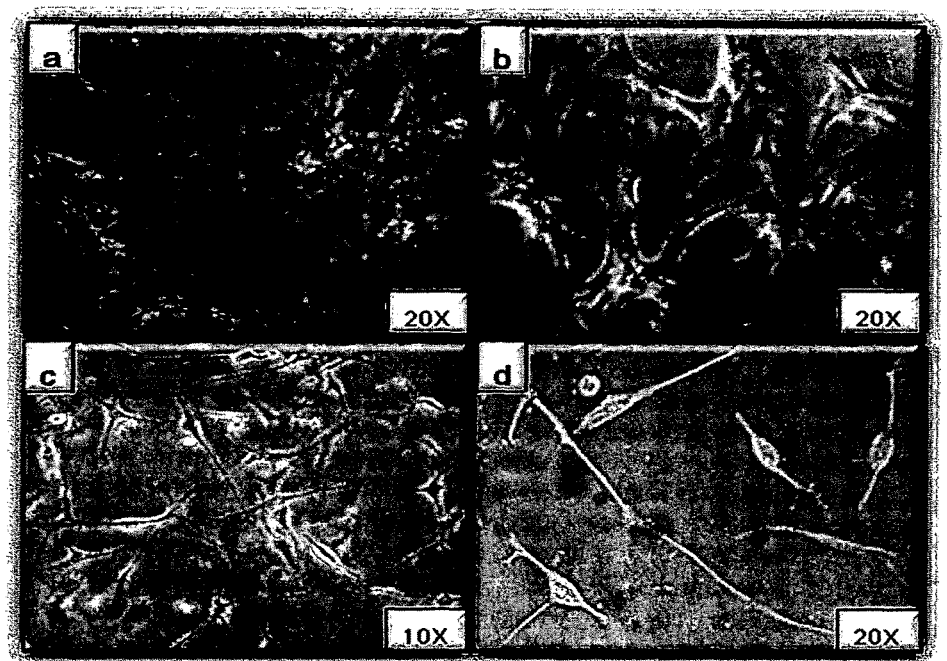
FIG. 2. Induction of neuronal differentiation of stem cells. OEGJ or an active fraction isolated from the OEGJ induced neuronal differentiation of mesenchymal stem cells (MSCs) in vitro. (a) Photomicrograph showing undifferentiated MSC morphology appearing as flat, irregular, and asymmetrical cells, which, upon treatment of the active fraction/OEGJ for two days; (b) cells become more condensed, refractive, star-like with branches under phase contrast microscope; (c) four to six days treatment of the MSCs, the MSCs differentiated into neuronal-like cells with a small cell body and sprouted neurites-like projections; and (d) an amplified photomicrograph showing neuronal differentiation of MSCs.

The present inventors further discovered that the extract not only enhanced the survival of neurons by protecting them from ischemia and stress, but also promoted the proliferation and differentiation of vessel endothelial cells in vitro (FIG. 1) and helped restore the blood perfusion of the ischemic brain. Furthermore, the inventors found that an active fraction obtained from this extract can also induce neuronal differentiation of mesenchymal stem cells (MSCs) in vitro (FIG. 2).

In accordance with one aspect, the invention provides methods of treating or preventing stroke or stroke complications of a subject in need thereof, which comprises administering to the subject an effective amount of a compound, composition, active fraction, or extract described herein.

The effects of stroke or stroke complications, which are improved by the extract can be one or more of increased microcirculation, disappearance of microclots, and improved blood perfusion to the brain. In one embodiment, the methods for the prevention or treatment of stroke include administering to a mammal in need thereof agents, active fractions, and/or extracts and compounds, and derivatives of such compounds from a variety of plants including *Geum japonicum*.

In another aspect, an agent for the treatment or prevention of stroke is part of a pharmaceutical composition containing one or more excipients, carriers, or fillers. In one embodiment, the pharmaceutical composition is packaged in unit dosage form. The unit dosage form is effective in improving microcirculation in the brain (e.g., increased microcirculation, disappearance of microclots, and improved blood perfusion) when administered to a subject in need thereof.

In various embodiments of the invention, suitable in vitro or in vivo assays are performed to determine the effect of an agent (extracts, fractions, and compounds) of the invention and whether its administration is indicated for the treatment or prevention of stroke in a subject. In some embodiments, in vivo models of stroke are used to assess the effects of an agent on a subject.

Methods and Compositions for the Prevention or Treatment of Dementia

Dementia is a progressive and irreversible disease of the brain in which the degeneration of brain cells causes thinking ability and memory to deteriorate. The most common types of dementia include Alzheimer's disease (AD), vascular dementia (VD), dementia with Lewy bodies, frontotemporal dementia, and mild cognitive impairment (MCI). AD is the most common type of dementia and the underlying cause of 60-80% of all dementia cases. Amyloid plaques are clearly visible in AD brains (Selkoe, 1991). Amyloid plaques, found outside and around neurons, are mostly formed by insoluble deposit of amyloid beta (Aβ) protein, a fragment from a larger protein called amyloid precursor protein (APP), critical to neuron growth, survival and post-injury repair (Glenner G G & Wong C W, 1984). The characteristics of AD are the extensive loss of neurons and synapses in the cerebral cortex and hippocampus. Compared to normal brains, AD brains show extreme shrinkage of cerebral cortex and hippocampus. The cholinergic basal forebrain neurons, which innervate the cerebral cortex and hippocampus, play a key role in cognition and memory. In the early stages of AD, the most commonly recognized symptom is memory loss, especially the loss of short-term memory. It has been suggested that initial atrophy of the cholinergic neurons in these two regions results in mild cognitive impairment (MCI) and their consequent degeneration results in AD. MCI is the stage between normal forgetfulness due to aging and the development of dementia.

Vascular dementia (VD) is usually caused by an interruption in the supply of blood to specific parts of the brain. Vascular dementia also can occur when blood vessels in the brain narrow, reducing the amount of blood flow to those sections of the brain. A network of blood vessels called the vascular system supplies the brain with oxygen. If there is a blockage in the vascular system, or if it is diseased, blood is prevented from reaching the brain. As a result, cells in the brain die, leading to the symptoms of dementia, which differ among individuals depending on which area of the brain has been damaged. After AD, vascular dementia is the second leading form of dementia, accounting for up to 20% of all cases.

Dementia symptoms include difficulty with many areas of mental function, including language, memory, perception, emotional behavior or personality, and cognitive skills (such as calculation, abstract thinking, or judgment). The early symptoms of dementia can include language problems, such as trouble finding the name of familiar objects, misplacing items, getting lost on familiar routes, personality changes and loss of social skills, losing interest in things you previously enjoyed, etc. As the dementia becomes worse, symptoms are more obvious and interfere with the ability to take care of oneself.

Research points to cerebrovascular pathology as a significant factor in the development of AD (de la Torre, 2004; Bell & Zlokovic, 2009). Risk factors for AD reported from different epidemiological studies include congestive heart failure, myocardial infarction, cardiac arrhythmia, hypertension, atrial fibrillation, atherosclerosis, aging, ischemic stroke, head injury, and transient ischemic attack, all of which are vascular-related and reduce cerebral perfusion. It has been suggested that chronic brain hypoperfusion (CBH) is a risk factor for AD. CBH has been found as a precipitant of MCI, and as the most effective predictor for the later development of AD (de la Tone, 2006). In the compromised or older individual, CBH leads to progressive metabolic changes on a subcellular level within particular brain regions, such as hippocampal and parietal regions, which cause a neurodegenerative state and elicit dementia. In supporting of the notion that AD is primarily a vascular disease, it has been reported that omental transposition directly to the brain of AD patients provided subjective and objective improvement, especially the functional status of the patients (Goldsmith et al., 2003). Previous research shows that cerebral blood flow to both cerebral hemispheres was significantly increased after intact omentum was placed directly on the brain of animals and humans (Goldsmith et al., 1990). The blood flow from the omentum perfused into the brain through numerous blood vessels that grew through the omental-cerebral interface after which these vessels penetrated vertically and deeply into the brain (Goldsmith, 2001). Therefore, the improvements seen in AD patients after omental transposition are likely due to the increase of cerebral blood flow.

The present inventors discovered that the compositions of the invention, including OEGJ, significantly promote physical reconstitution of the insufficient blood supply to the brain that will substantially improve the living micro-environment of neurons; enhance cell survival that will protect neurons from ischemic and stress insults; and induce neuronal differentiation of mesenchymal stem cells (MSCs) in vitro that may be translated into neuronal regeneration. Based on the vascular and neuronal beneficial effects of OEGJ and the pathophysiology of dementia, OEGJ can increase blood supply to the brain, enhance neuron survival and neuronal regeneration, and thus improve learning and memory of AD and VD subjects.

In accordance with one aspect, the invention provides methods of treating or preventing dementia, including Alzheimer's disease, in a subject in need thereof, which comprises administering to the subject an effective amount of a compound, composition, active fraction, or extract described herein. The effects of Alzheimer's disease or symptoms thereof to be improved can be one or more of APP-positive staining in the hippocampal and neocortical areas; increased tau-2 staining in the cortex, corpus callosum, and hippocampus; reactive microglia and astrocytes in the corpus callosum, cingulate gyms, thalamus, and cortex; increased expression of TNF-α and NF-κB in the cortex and corpus callosum; increased proliferation of microglia surrounding the lateral ventricles and in the corpus callosum; deposits of congophilic A in the wall of the lateral ventricle and CA1 hippocampus; lesions in the fornix, anterior hippocampus, and CA1 hippocampus; and memory deficit. These pathological and inflammatory signs and symptoms are characteristic of Alzheimer's disease in humans. In one aspect, the methods for the prevention or treatment of Alzheimer's disease include administering to a mammal in need thereof agents, active fractions, and/or extracts and compounds, and derivatives of such compounds from a variety of plants including *Geum japonicum*.

In various embodiments of the invention, suitable in vitro or in vivo assays are performed to determine the effect of an agent (extracts, fractions, and compounds) of the invention and whether its administration is indicated for treatment or prevention of Alzheimer's disease in a subject.

Methods and Compositions for the Prevention or Treatment of Parkinson's Disease

Parkinson's disease (PD) is a neurodegenerative disorder that affects the basal ganglia of central nervous system, mainly a region named the subtantia nigra (Lees et al., 2009). Neurons in the subtantia nigra normally produce neurotransmitter dopamine, and project to the striatum, the largest component of basal ganglia. The loss of dopaminergic neurons in the subtantia nigra, a hallmark of PD, leads to insufficient supply of dopamine in the striatum which results in changes of the activity of the neural circuits within the basal ganglia which coordinates muscle movements. As a result, movement in PD patients is affected. Characteristic symptoms seen in PD patients include involuntary trembling of the limbs, muscle rigidity, lack of movement or slowness in initiating and maintaining movement, and postural instability. PD is a progressive disease so that the symptoms worsen over time (Halliday & McCann, 2010).

Secondary symptoms, such as cognitive impairment, behavior and speech problems, may also occur in PD patients, especially those with advanced PD. Cognitive impairments, such as dementia, afflict a majority of patients as the disease advances (Leverenz et al., 2009). The cognitive defects of PD vary from subtle executive dysfunction in the early stages of the disease to dementia in the advanced states. A person with PD has six-fold increased risk of developing dementia. Several studies have shown that the point prevalence for dementia in PD can reach between 28% and 44% (Mayeux et al., 1992; Aarsland et al., 1996; Hobson & Meara, 2004). Disrupted blood supply in the substantia nigra due to age, stroke and arteriosclerosis will deprive the dopaminergic neurons in this area of sufficient supply of oxygen and nutrients that eventually lead to cell death In accordance with one aspect, the invention provides methods of treating or preventing Parkinson's disease in a subject in need thereof, which comprises administering to the subject an effective amount of a compound, composition, active fraction, or extract described herein. The effects of Parkinson's disease or symptoms thereof to be improved can be one or more of rigidity, tremors, slowed movements, impaired balance, and loss of dopaminergic neurons. In one aspect, the methods for the prevention or treatment of Parkinson's disease include administering to a mammal in need thereof agents, active fractions, and/or extracts and compounds, and derivatives of such compounds from a variety of plants including *Geum japonicum*. In another aspect, an agent for the treatment or prevention of Parkinson's disease is part of a pharmaceutical composition containing one or more excipients, carriers, or fillers. In one embodiment, the pharmaceutical composition is packaged in unit dosage form. The unit dosage form is effective in improving rigidity, tremors, slowed movements, impaired balance, and loss of dopaminergic neurons when administered to a subject in need thereof when administered to the subject.

In various embodiments of the invention, suitable in vitro or in vivo assays are performed to determine the effect of an agent (extracts, fractions, and compounds) of the invention and whether its administration is indicated for the treatment or prevention of Parkinson's disease in a subject. In some embodiments, in vitro models of Parkinson's disease are used to assess the effects of an agent on a subject.

Methods and Compositions for the Prevention or Treatment of Chronic Cerebral Ischemia Cerebral blood flow refers to the blood supply to the brain at any given time. It is well-known that a sudden disruption of the blood supply to the brain leads to stroke. On the other hand, chronic cerebral ischemia, also known as chronic cerebral hypoperfusion, refers to the condition when reduction of the cerebral blood flow is moderate but persistent and is too low to meet the metabolic demands of brain tissue. Once brain tissue becomes ischemic, a biochemical cascade known as the ischemic cascade is triggered which would cause damage and eventual death of brain cells.

Aging is considered a common factor that leads to chronic cerebral ischemia. Significant functional and structural abnormalities occur in human vasculature with advancing of age. The most common aging related vascular change is the gradual thickening and hardening of the walls as well as narrowing of the lumen of the vessels. The overall consequence is a progressive reduction or even a complete cessation of blood flow to the affected brain region. It has been reported that cerebral blood flow exhibits a significant yearly decrease with age (Frackowiak et al., 1980; Buijs et al., 1998). According to a more recent study, the mean total cerebral blood flow in elderly subjects is about ⅓ lower than that in healthy young subjects (Spilt et al., 2005). Chronic cerebral ischemia is also linked to many pathophysiological factors. Some possible causes of cerebral ischemia include heart failure, atherosclerosis-related or amyloid plaque-related narrowing of cerebral arteries, impaired endothelium-dependent vasodilation and cerebral small vessels disease (Spilt et al., 2005). Symptoms of chronic cerebral ischemia include headache, dizziness, hypertension, seizures, and neurological deficits.

In addition to neurodegenerative disorders, cerebral ischemia has also been identified as the principal pathogenetic mechanism underlying most of the neuropathology attributed to cerebral hypoxia-ischemia in the neonate. Cerebral hypoxia-ischemia is most likely to occur as a consequence of interruption in placental blood flow and gas exchange. Hypoxic-ischemic cerebral injury that occurs during the perinatal period is one of the most commonly recognized causes of severe, long-term neurologic deficits in children (Perlman, 1997). Since cerebral ischemia has been identified as a critical trigger for neurodegenerative disorders, the improvement of cerebral blood flow is predicted to moderate the symptoms and to delay the onset of the related disorders.

The present inventors have discovered that OEGJ treatment substantially improves the blood supply to the ischemic regions of the brain and the living micro-environment of neurons. More importantly, the present inventors have further demonstrated the remarkable usefulness of OEGJ in treating chronic brain ischemia in humans. In one embodiment, 2-4 weeks treatment with OEGJ (2-3 grams/day) can nearly cure the manifestations of the patients.

Formulations and Dosages of Pharmaceutical Compositions

In various embodiments of the invention, suitable in vitro or in vivo assays are performed to determine the effect of an agent (extracts, fractions and compounds) of the invention and whether its administration is indicated for treatment of the affected disease or medical condition in a subject. Examples of these assays are described above in connection with a specific disease or medical treatment.

Typically, an effective amount of the compositions of the present invention, sufficient for achieving a therapeutic or prophylactic effect, range from about 0.000001 mg per kilogram body weight per day to about 10,000 mg per kilogram body weight per day. Suitably, the dosage ranges are from about 0.0001 mg per kilogram body weight per day to about 2000 mg per kilogram body weight per day. An exemplary treatment regime entails administration once every day or once a week or once a month. The agent usually administered on multiple occasions. Intervals between single dosages can be daily, weekly, monthly or yearly. Alternatively, the agents can be administered as a sustained release formulation, in which case less frequent administration is required. Dosage and frequency vary depending on the half-life of the agent in the subject. The dosage and frequency of administration can vary depending on whether the treatment is prophylactic or therapeutic. In prophylactic applications, a relatively low dosage is administered at relatively infrequent intervals over a long period of time. Some subjects continue to receive treatment for the rest of their lives. In therapeutic applications, a relatively high dosage at relatively short intervals is sometimes required until progression of the disease is reduced or terminated, and preferably until the subject shows partial or complete amelioration of symptoms of disease. Thereafter, the patent can be administered a prophylactic regime.

Toxicity.

Suitably, an effective amount (e.g., dose) of an agent described herein will provide therapeutic benefit without causing substantial toxicity to the subject. Toxicity of the agent described herein can be determined by standard pharmaceutical procedures in cell cultures or experimental animals, e.g., by determining the $LD_{50}$ (the dose lethal to 50% of the population) or the $LD_{100}$ (the dose lethal to 100% of the population). The dose ratio between toxic and therapeutic effect is the therapeutic index. The data obtained from these cell culture assays and animal studies can be used in formulating a dosage range that is not toxic for use in human. The dosage of the agent described herein lies suitably within a range of circulating concentrations that include the effective dose with little or no toxicity. The dosage can vary within this range depending upon the dosage form employed and the route of administration utilized. The exact formulation, route of administration and dosage can be chosen by the individual physician in view of the subject's condition. See, e.g., Fingl et al., In: *The Pharmacological Basis of Therapeutics*, Ch. 1 (1975).

According to the methods of the present invention, the agents can be incorporated into pharmaceutical compositions suitable for administration. In some embodiments, the pharmaceutical compositions may comprise purified or substantially purified extracts of *Geum japonicum* and a pharmaceutically-acceptable carrier in a form suitable for administration to a subject. In other embodiments, the pharmaceutical compositions may comprise pharmaceutically-acceptable carriers are determined in part by the particular composition being administered, as well as by the particular method used to administer the composition. Accordingly, there is a wide variety of suitable formulations of pharmaceutical compositions for administering the compositions (see, e.g., *Remington's Pharmaceutical Sciences*, Mack Publishing Co., Easton, Pa. 18$^{th}$ ed., 1990). The pharmaceutical compositions are generally formulated as sterile, substantially isotonic and in full compliance with all Good Manufacturing Practice (GMP) regulations of the U.S. Food and Drug Administration.

The terms "pharmaceutically-acceptable," "physiologically-tolerable," and grammatical variations thereof, as they refer to compositions, carriers, diluents and reagents, are used interchangeably and represent that the materials are capable of administration to or upon a subject without the production of undesirable physiological effects to a degree that would prohibit administration of the composition. For example, "pharmaceutically-acceptable excipient" means an excipient that is useful in preparing a pharmaceutical composition that is generally safe, non-toxic, and desirable, and includes excipients that are acceptable for veterinary use as well as for human pharmaceutical use. Such excipients can be solid, liquid, semisolid, or, in the case of an aerosol composition, gaseous. A person of ordinary skill in the art, would have no difficulty determining the appropriate timing, sequence and dosages of administration for particular drugs and compositions of the present invention.

Suitable examples of such carriers or diluents include, but are not limited to, water, saline, Ringer's solutions, dextrose solution, and 5% human serum albumin. Liposomes and non-aqueous vehicles such as fixed oils may also be used. The use of such media and compounds for pharmaceutically active substances is well known in the art. Except insofar as any conventional media or compound is incompatible with the agent, use thereof in the compositions is contemplated. Supplementary active compounds can also be incorporated into the compositions.

A pharmaceutical composition of the invention is formulated to be compatible with its intended route of administration. The compositions of the present invention can be administered by parenteral, topical, intravenous, oral, subcutaneous, intra-arterial, intradermal, transdermal, rectal, intracranial, intraperitoneal, intranasal; intramuscular route or as inhalants. The agent can optionally be administered in combination with other agents that are at least partly effective in treating various diseases.

Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial compounds such as benzyl alcohol or methyl parabens; antioxidants such as ascorbic acid or sodium bisulfite; chelating compounds such as ethylenediaminetetraacetic acid (EDTA); buffers such as acetates, citrates or phosphates, and compounds for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, e.g., water, ethanol, polyol (e.g., glycerol, propylene glycol, and liquid polyethylene glycol, and the like), and suitable mixtures thereof. The proper fluidity can be maintained, e.g., by the use of a coating such as lecithin, by the maintenance of the required particle size in the case of dispersion and by the use of surfactants. Prevention of the action of microorganisms can be achieved by various antibacterial and antifungal compounds, e.g., parabens, chlorobutanol, phenol, ascorbic acid, thimerosal, and the like. In many cases, it will be preferable to include isotonic compounds, e.g., sugars, polyalcohols such as manitol, sorbitol, sodium chloride in the composition. Prolonged absorption of the injectable compositions can be brought about by including in the composition a compound which delays absorption, e.g., aluminum monostearate and gelatin.

Sterile injectable solutions can be prepared by incorporating the agents in the required amount in an appropriate solvent with one or a combination of ingredients enumerated above, as required, followed by filtered sterilization. Generally, dispersions are prepared by incorporating the binding agent into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof. The agents of this invention can be administered in the form of a depot injection or implant preparation which can be formulated in such a manner as to permit a sustained or pulsatile release of the active ingredient.

Oral compositions generally include an inert diluent or an edible carrier. They can be enclosed in gelatin capsules or compressed into tablets. For the purpose of oral therapeutic administration, the binding agent can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding compounds, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating compound such as alginic acid, Primogel, or corn starch; a lubricant such as magnesium stearate or Sterotes; a glidant such as colloidal silicon dioxide; a sweetening compound such as sucrose or saccharin; or a flavoring compound such as peppermint, methyl salicylate, or orange flavoring.

In one embodiment, the agents are prepared with carriers that will protect the agent against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically-acceptable carriers. These can be prepared according to methods known to those skilled in the art, e.g., as described in U.S. Pat. No. 4,522,811.

EXAMPLES

The present technology is further illustrated by the following examples, which should not be construed as limiting in any way.

Example 1—Isolation of an Active Extract from *Geum Japonicum*

For the experiments disclosed in the following examples, the extract was obtained from the plant *Geum japonicum*. The plant was collected from Lushan, Jiangxi Province of China in July was dried (50 kg) and percolated with 80% ethanol (500 L) at room temperature for 3 days twice. The extract was combined and spray-dried to yield a solid residue (5 kg). The solid residue was suspended in 10 volumes $H_2O$ and successively partitioned with 10 volumes of hexane and chloroform twice. Next, 70% ethanol (10 volumes) was used to recover the remaining twice. The ethanol soluble fraction was filtered and spray dried to yield a powder fraction.

Neuronal Differentiation of Mesenchymal Stem Cells.

A bio-assay guided strategy was used for screening plant constituents to identify the composition of compounds showing dual actions for promoting angiogenesis and inducing neuronal differentiation of stem cells. During the screening of the plant extract for induction of the expected dual actions, an organic extract of *Geum japonicum* (OEGJ) was identified. It was found that OEGJ could significantly enhance the proliferation at low concentration. At higher concentration, the extract induced differentiation of Human Umbilical Vein Endothelial Cells in vitro (HUVEC) (FIG. 1) and neuronal differentiation of mesenchymal stem cells in vitro (FIG. 2). When the extract (200 μg/ml) was added to mesenchymal stem cell culture, it was found that approximately ~10% of the flattened asymmetrically and irregularly-shaped rat bone marrow-derived MSC was induced to differentiate to condensed, refractive and branched cells 3 days after treatment with the extract. Furthermore, these refractive and branched cells differentiated into the neuronal-like cells with a small condensed cell body and multi/long dendrites-like extensions 8 days after treatment with the extract. Thus, OEGJ has the ability to prime the MSC along the neurogenic differentiation lineage. Therefore, it may promote neuronal regeneration to replace damaged neurons in stroke, Alzheimer's disease (AD), Parkinson's disease and vascular dementia.

Biostatistics.

All morphometric data were collected blindly. Results are presented as mean±SD computed from the average measurements obtained from each heart. Statistical significance for comparison between two measurements was determined using the unpaired two-tailed Student's t test. Values of P<0.05 were considered to be significant.

Example 2—Effects of OEGJ in Treating Ischemic Stroke

All protocols used in the examples conformed to the Guide for the Care and Use of Laboratory Animals published by the U.S. National Institutes of Health, and was approved by the Animal Experimental Ethical Committee of The Zhangjiang Hightech park.

Animal Models of Ischemic Stroke and Treatment Protocol.

Ischemic stroke was induced in SD rats by surgery according to the methods used previously (Mayzel-Oreg et al., 2004; Steiner et al., 1980). Briefly, the common carotid artery (CCA), internal carotid artery (ICA), and external carotid artery (ECA) around the carotid bifurcation were exposed through a midline incision in the right side of the neck. CCA was ligated proximal to the carotid bifurcation. Saline solution (0.5 ml) containing ~1000 microspheres (80-150 μM) was injected by a syringe inserted into the ECA pointing toward the carotid bifurcation. After ligation of the ECA distal to the injection site and removal of CCA ligation, the injected microspheres entered the ICA resulted in multi-infarct ischemic stroke in the brain. One day after the surgery, neurological status of animals was evaluated according to a neurological grading system developed by Benderson et al. (Benderson et al., 1986). Rats were then divided into two groups according to the grades assigned so that rats in each group had an overall similar grade. Test group (n=12) was treated with OEGJ for 4 weeks (oral administration 480 mg OEGJ in water/kg body weight). An equivalent number of animals in the vehicle-treated group (n=16) was orally administered with the same volume of water. The reason for more rats in vehicle treated control group is the higher death rate in the vehicle-treated control group.

Following the surgically induced stroke, both vehicle treated control rats and those that received OEGJ treatment were evaluated for their motor and neurological performance. For instance, adult animals were tested across a range of standardized tasks after undergoing the surgically induced stroke. Improvements in OEGJ-treated animals included enhanced performance across the range of tests, which examined strength, balance, agility and fine motor skills, and also included greater recovery of injured tissue.

Ultrasound Doppler Velocity Assessment of the Blood Flow of Basal Artery.

Blood flow velocity (BFV) from the concerned arteries was measured using ultrasound Doppler Velocity during the experiment post-ligation. Ultrasound measurement of brain flow velocity helps provide information on the redistribution of the blood flow supply after the onset of stroke. It was found that the percent reduction of BFV in right CCA was between 20-53% of the control at 6 h after surgery-embolism. The BFV tended to recover 1 week after surgery except for the regions of neuronal damage. These results indicated that neuronal damage did not correlate with the flow rate. Since increase of blood flow to the ischemic brain through induction of growth of new collateral vessels is one of the most critical steps for the substantial treatment of stroke, therefore, in the present study, we used a brain ischemia rat model by permanent ligation of bilateral common carotid arteries. Bilateral carotid artery ligation (BCAL) in SD rats was studied. The death rate of the surgery procedure within one week was about 20%. The 12 survivors were divided into test group (n=6) and control group (n=6). The rats in test group were orally administered OEGJ (480 mg/kg) for 5 weeks and the rats in vehicle-treated control group were equivalently administered water.

Figure 3:
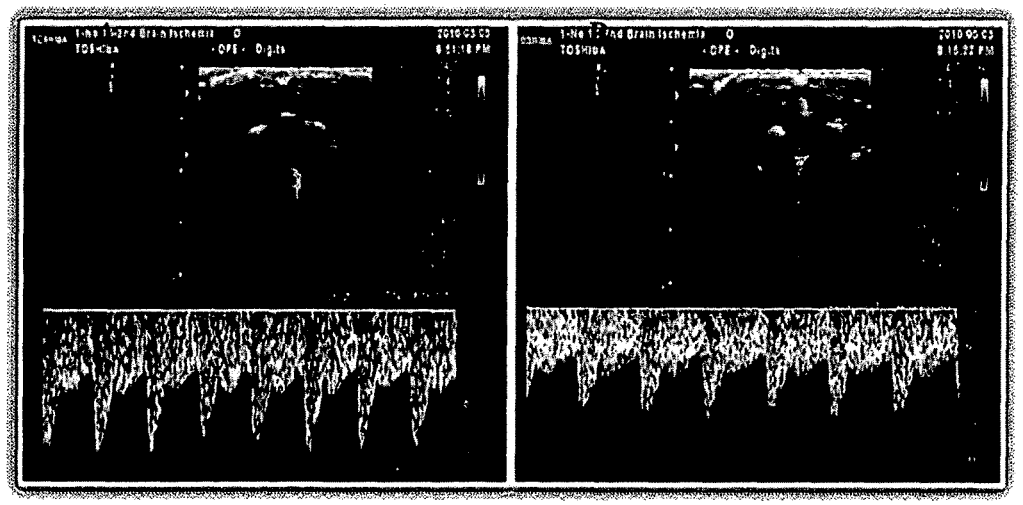
FIG. 3. The ultrasound Doppler velocity demonstration of the increased brain blood flow induced by OEGJ treatment. (a) The cerebral blood flow velocity of the vehicle-treated rats 5 weeks after BCAL; and (b) the cerebral blood flow velocity of the OEGJ-treated rats 5 weeks after BCAL. It was shown that the cerebral blood flow volume is significantly higher in OEGJ-treated rats.

The BFV of the basal artery of the experimental rats was studied. The rationale for considering only the BFV measurements of basal artery was that this vessel contributes maximally to collateral pathways in bilateral carotid occlusive disease. The BFV of basal artery was measured with a 12-MHz linear probe of the Toshiba ultrasound scanner at week 5 during OEGJ treatment. The average of 3 repeated measurements was taken as the BFV of an artery. The presence of intracranial collateral circulation was confirmed by histopathological studies. It was found that to compensate the reduced blood flow volume due to BCAL, which normally contributes to 60% blood flow volume to the brain, the systemic blood pressure significantly increased by 25% of the normal blood pressure in order to pump about 30% more blood of normal basal blood volume to the brain as determined by ultrasound Doppler Velocity (FIG. 3). By contrast, in the rats of OEGJ-treated group, not only did the blood pressure remain normal, but also the blood flow volume increased by about 90% of the normal basal blood volume to the brain, which accounts for 76% of the normal total blood volume to the brain (FIG. 3). To rule out the possibility of vessel dilation effect of OEGJ, after 5 weeks treatment of OEGJ, the administration of OEGJ was terminated. The blood flow volume was determined again 2 weeks after the termination of OEGJ treatment. Similar results to those obtained at week 5 during the OEGJ treatment were attained, indicating that OEGJ treatment induced growth of new collateral vessels in brain that would reduce the peripheral resistance of arterioles or micro-vessels so that significant more blood flow volume to the brain is achieved without elevation of blood pressure.

OEGJ-Induced Neovascularization in the Stroke Brain.

Figure 4:
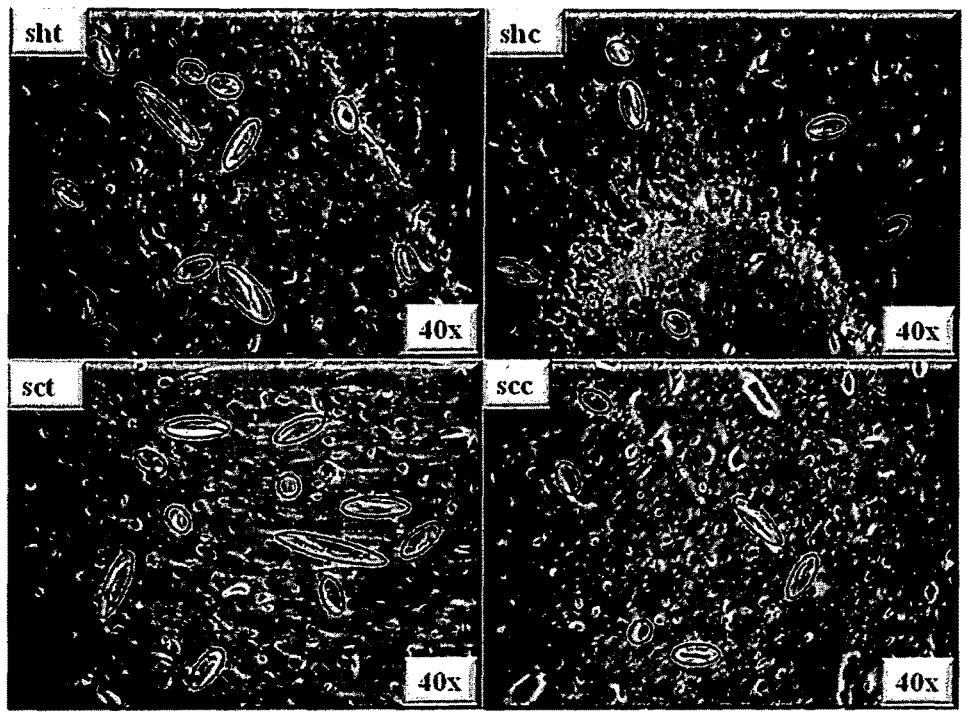
FIG. 4. The induced angiogenesis/neovascularization in ischemic stroke brain following OEGJ treatment. (sht) Significantly more blood vessels (circled) were observed around the region of hippocampus in OEGJ-treated animals; (shc) by contrast, fewer vessels were observed around hippocampus region in vehicle-treated rats (circled); (sct) more vessels were observed in the region of cortex of frontal lobe in OEGJ-treated rats (circled); and (scc) fewer vessels were found in the same region in vehicle-treated animals (circled).

Brains from the stroke rats sacrificed 7 weeks post surgery were removed, fixed in formalin and embedded in paraffin. Thin sections (5 µm thick) were cut from each slide and stained with H&E staining. The vascular density was determined on the histology section samples by counting the number of vessels within the cortex of frontal lobe and around the regions of hippocampus using a light microscope under a high power field (HPF) (40×). Six random and non-overlapping HPFs within the frontal lobe or around the regions of hippocampus were inspected for counting all the vessels in each section. The number of vessels in each HPF was averaged and expressed as the number of vessels per HPF. Vascular counts were performed by two investigators in a blind fashion. It was found that the numbers of vessels are about 51.16±16/HPF in the regions of cortex in frontal lobe and 61.66±21/HPF around the regions of hippocampus in OEGJ-treated rats (FIG. 4). By contrast, the numbers of vessels are about 34.2±12/HPF in regions of cortex in frontal lobe and 38.5±7.5/HPF around the regions of hippocampus in vehicle-treated rats (FIG. 4).

Regeneration of Neurons.

Figure 5:
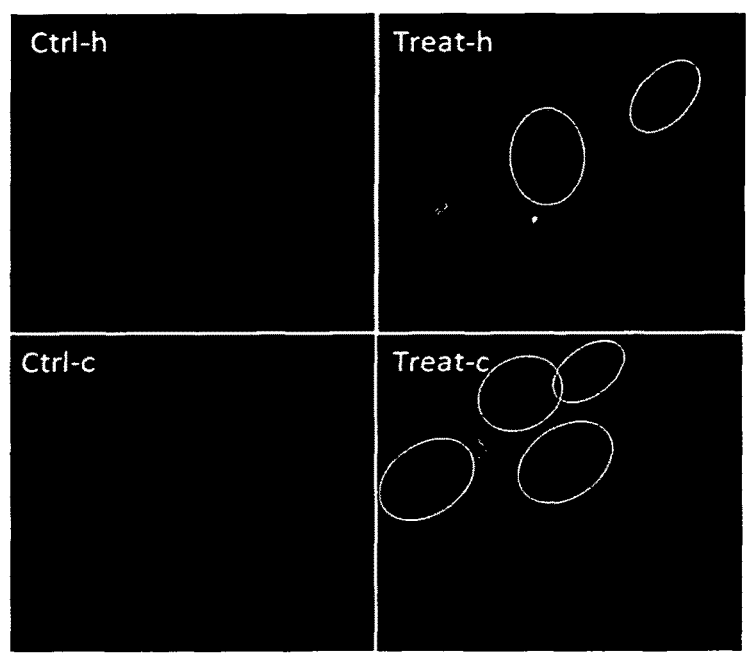
FIG. 5. The induced-neuronal regeneration in ischemic stroke brain. (Ctrl-h) Almost no positive green fluorescence signals (nestin immunohistochemical staining) were observed in the hippocampus region of vehicle-treated rats; (Treat-h) some nestin-positive green fluorescence signals (circles) with the shape of neurons and nuclei negatively stained were detected in the region of the hippocampus in OEGJ-treated animals indicating neuronal regeneration; (Ctrl-c) almost no nestin positive green fluorescence signals were found in cortex region of frontal lobe of vehicle-treated rats; and (Treat-c), some nestin-positive green fluorescence signals (circles) were identified in cortex region of frontal lobe in OEGJ-treated rats.

Thin sections (5 µm thick) were cut from each slide and immune-histochemically stained with specific antibodies against Ki67 and Nestin. The Ki67 protein is a cellular marker for proliferation, which is strictly associated with cell proliferation. During interphase, the Ki-67 antigen can be exclusively detected within the cell nucleus, whereas in mitosis most of the protein is relocated to the surface of the chromosomes. Ki-67 protein is present during all active phases of the cell cycle ($G_1$, S, $G_2$, and mitosis), but is absent from resting cells ($G_0$). Nestin is a 200-220 kDa major intermediate filament (IF) protein of embryonic central nervous system progenitor cells. Nestin is a marker for neuroepithelial stem cells during rapid growth. During axon elongation of some neurons, nestin localizes to the growth cones and may play a role in growth cone guidance. Therefore, we used Ki67 and Nestin as the markers of neuronal regeneration in brain. On microscope examination of the sections, multi-infarcted regions were found throughout the entire brain, such as in frontal lobe, hippocampus, temporal lobe and parietal lobe. It was also found that OEGJ treatment not only stimulated growth of new cerebral collateral vessels (FIG. 4), but also induced neuronal regeneration in cortex of frontal and parietal lobes and in hippocampus as indicated by Ki67 and nestin immunohistochemical staining (FIG. 5). By contrast, no significant growth of the new collateral vessels in the brain (FIG. 4) was identified and neither significant regeneration of new neuron cells in the non-treated control brains (FIG. 5). In sum, these observations imply that OEGJ not only stimulated the substantial growth of new collateral vessels in ischemic brain, but also induced neuronal regeneration in many regions of the affected brains replacing the died neurons.

The most critical steps for substantial treatment of ischemic stroke are the reconstitution of blood supply to restore the microenvironment for neural cells to live and function, and regeneration of neurons to replace dead neuronal cells. These results demonstrate that OEGJ satisfies these two requirements; hence, it can be used for the treatment of ischemic stroke.

Example 3—Treatment of Severe Human Ischemic Stroke Patients with OEGJ

Based on above rather promising results from the OEGJ-enhanced differentiation of vessel endothelial cells and substantial growth of new collateral vessels in ischemic brain, and OEGJ-induced neuronic differentiation of MSCs in vitro and substantial therapeutic effects in an animal model, the potential as to whether the OEGJ-mediated substantial therapeutic effect observed in a stroke animal model could be successfully used in a clinical setting was tested in stroke patients on the basis of mercy treatment. Our preliminary clinical test was conducted with ischemic stroke patients (2 female patients and 2 male patients) with their family member's full awareness and written consent.

One female patient from Taiwan had a severe ischemic stroke about two years before treatment showing complete loss of language ability, inability to walk or stand, loss of almost all other physical abilities, such as self-eating, moving arms or legs. The cognitive impairment was severe, such that she was unable to understand even very simple language or gestures and recognize familial members or familiar things, thus appearing nearly as a vegetative patient. However, during two months of OEGJ treatment (oral administration, 2 grams/day), her language ability, the ability to remember names and identities of her family members and some of her physical abilities were gradually restored. Furthermore, the treatment also significantly improved her vision and restored some of the cognitive abilities, such as learning to play electronic mahjong and making phone calls.

Another female patient from Shanghai had her first brain attack about two years before treatment with significant cognitive impairment, such as problems remembering the identities of herself and her family members. She was also unable to rest with physical activities unimpaired or hyperactivity. She appeared unable to focus attention and was easily distracted. After she had another brain attack about 8 months before the OEGJ treatment, she completely lost her language and all physical abilities. She lost any proactive reaction to events and appeared as a complete vegetative patient with muscle stiffness, deep and large decubitus ulcer (16 cm diameter and 10 cm deep) and severe insomnia at the time of examination. Interestingly, two months of OEGJ treatment (oral administration, 2 grams/day) completely healed her deep decubitus, substantially restored her insomnia to a normal sleep pattern, remarkably restored her language ability for normal and complicated communication, and the ability in finding names and identities of her family members. Significant improvement of her physical ability and vision were also reported.

Another male patient from Beijing had a brain attack about 6 months prior to treatment. About 6 months before the brain attack happened to him, he already had the warning symptoms of brain ischemia, such as, headache, dizziness and inability to focus on work or writing in the afternoon. After the stroke, he recovered from the acute phase of the brain attack, but he complained of difficulty in language expression, headache and soreness at the part of infarcted area of his brain. Physically, he could not walk fast, or else he would lose his body stability. He could not focus his attention on work or writing any more. After two months' treatment with OEGJ (2 g/daily, oral administration), his blood pressure returned to normal, the sore feeling of the part of brain infarction was dissolved; and the complexion of his face looked healthier. Most importantly, he could focus on working or writing again for whole day, which was even better than before his brain attack. Physically, he could walk fast while keeping good body stability and balance. He appears completely normal.

Example 4—OEGJ Promotes Cerebral Blood Flow

Our preliminary studies and studies from other researchers (Farkas et al., 2007) have suggested that chronic ischemia in the forebrain may be one of the major causes for AD, VD and other cognitive disorders in humans. In order to explore the possible beneficial usefulness of OEGJ in promoting CBF, we used a rat model with chronic ischemia in the forebrain, hippocampus and other lobes of the brain by permanent bilateral common carotid arteries occlusion (2VO), which resembles brain ischemia in humans having the symptoms of learning and memory deficiency, and cognitive impairment.

Male Sprague-Dawley (SD) rats, weighing 250-300 g were used. The study was conducted in accordance with the National Regulations of Experimental Animal Administration, and all animal experiments were approved by the Committee of Experimental Animal Administration of Zhangjiang High-tech Park. For chronic bilateral occlusion (n=12), both of the left and right common carotid arteries were exposed through a midline cervical incision under anesthesia and then they were ligated by 6-0 nylon suture respectively, and cut by microscissors. The wound was thereafter closed with a suture. After recovering from anesthesia, the experimental animals were allowed free access to food and water.

The rats (n=6) in the OEGJ treatment group were intragastricly administered daily with an OEGJ suspension (480 mg/kg/day in water) from day 1 to day 30. The animals in the vehicle treatment group (n=6) were administered an equal volume of water daily for an equal period. The rats were analyzed after they had been on the treatment for 1 month. The changes of brain blood flow were measured by a Toshiba Aplio XG ultrasound.

Figure 6:
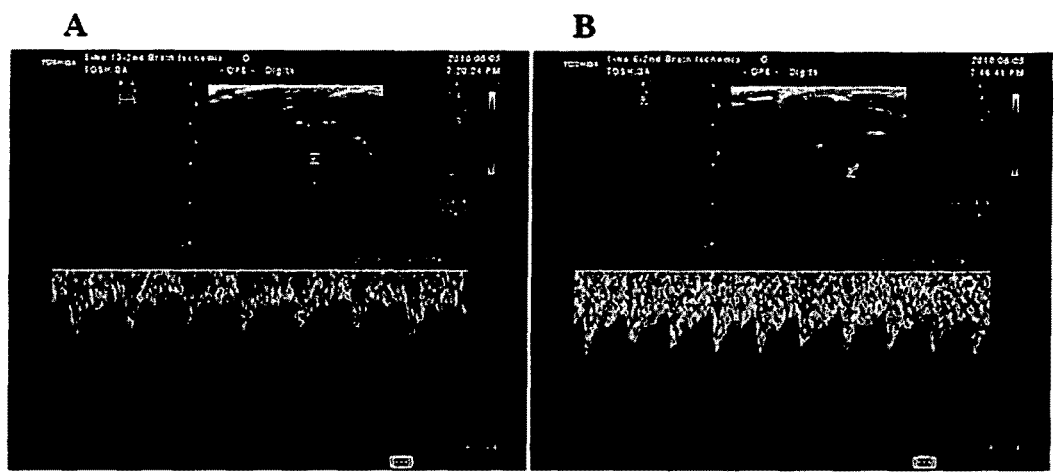
FIG. 6. Measurement of cerebral blood flow volume using ultrasound Doppler velocity. (A) the cerebral blood flow velocity of the vehicle-treated rats 30 days after 2VO; and (B) the cerebral blood flow velocity of the OEGJ-treated rats 30 days after 2VO. It was shown that the cerebral blood flow volume is significantly higher in OEGJ-treated rats.

The total cerebral blood flow volume was evaluated by measuring the basal artery of the experimental animals using a Toshiba Aplio XG ultrasound with PLT-1202S linear array transducer. Angle-corrected time averaged flow velocity and cross-sectional areas of vessels were measured. After 2VO of the rats, the blood supply to the brain depends predominantly on the basal artery, which normally supply approximately 40% of the total blood supply to the brain. The results showed that although the blood flow volume of the basal artery (BFV) in sham operated rats is around 13.81±4.21 ml/min, it reached 16.23±4.17 ml/min in vehicle-treated rats due to the compensation mechanism to the 2VO (FIG. 6). Interestingly, the BFV in OEGJ-treated animals increased up to 26.60±11.10 ml/min, which is about the 85% of the normal level of the total cerebral blood flow volume (FIG. 6). Furthermore, the blood pressure in vehicle-treated animals averaged around 154 mmHg, which is higher than that (around 125 mmHg) in sham operated animals. By contrast, the blood pressure in OEGJ-treated animals averaged 135 mmHg, which is significantly lower than that of vehicle-treated rats, but slightly higher than the level of sham-operated rats indicating brain collateral vessel formation that reduced the peripheral resistance of brain arteries or vessel dilation due to OEGJ treatment. To rule out the possibility of vessel dilation effect of OEGJ, we measured the BFV again in these experimental animals two weeks after OEGJ treatment. Similar results were attained. Namely, two weeks after termination of the OEGJ treatment, the BFV remained similar to the value of last measurement in OEGJ-treated rats with blood pressure approximately 128 mmHg. While in vehicle-treated rats, both the BFV and blood pressure were about the same to the values of last measurements two weeks earlier. In conclusion, the significantly decreased blood supply to the brain due to 2VO was restored by OEGJ treatment. Without wishing to be limited by theory, the underlying mechanism is probably due to the enhanced collateral vessel formation in ischemic brain that reduced the resistance of the arterioles of the brain, which was further confirmed by histological studies (blood vessel counting) of the same brain samples.

Example 5—OEGJ-induced Therapeutic Effects in Alzheimer's Disease Animal Models

The effects of OEGJ on two widely-used AD animal models were tested in this example: a transgenic mouse model that carries mutant genes for amyloid precursor protein (APP) and senescence accelerated mouse (SAM). APP mice develop fibrillar amyloid plaques and AD-like brain pathology, providing a valuable animal model to study AD. As the APP mice age, they exhibit impairments in spatial learning and memory. SAM mice, developed by Takeda and his colleagues (Takeda et al., 1991), show characteristics of rapid aging. They develop early abnormalities in learning and memory. These are related to abnormalities in hippocampal function. The SAM mice appear to be an excellent model to examine the pathophysiology of early defects seen in AD.

All studies were conducted in accordance with the National Regulations of Experimental Animal Administration, and all animal experiments were approved by the Committee of Experimental Animal Administration of Zhangjiang High-tech Park. Both APP and SAM mice (6 months old) were randomly divided into OEGJ-treated group (APP, n=15 and SAM, n=15) and vehicle-treated group (APP, n=14 and SAM, n=14). The mice in the OEGJ treatment group were intragastricly administered daily with an OEGJ suspension (480 mg/kg/day in water) for 30 days. The animals in vehicle treatment group were administered an equal volume of water daily.

OEGJ-Induced Improvement in Learning and Memory in SAMP10 Mice.

Figure 7:
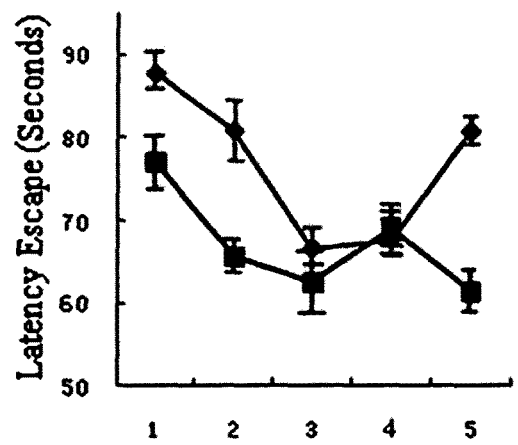
FIG. 7. Water maze assessment of spatial learning and memory capacity in SAMP10 mice. The training trials were carried out on day 30 after a month of OEGJ treatment. Every point in the figure represents the average of 4 times training. Animals were trained 4 times a day for 5 days. It was found that OEGJ-treated mice exhibited a significantly shorter escape latency compared to the vehicle-treated mice, $P<0.001$. There were significant group effects on the time spent in finding the hidden platform. Columns indicate mean±SD (n=30).

After one month OEGJ or vehicle treatment, the Morris water maze (1.8 M) was used in both OEGJ-treated group and vehicle-treated group to assess their spatial learning and memory capacity. Animals were trained 5 times a day for 4 days. The time spent prior to finding the hidden platform, also known as escape latency, was recorded. On the fifth day, the mice were subjected to a probe trial in which the platform was removed and their memory for platform location was assessed. Typically, time spent in the target quadrant (where the platform was previously located) was used to assess the strength of the memory of the mouse for the platform location. The average swim distance from the previous platform location and the number of crossings over the exact location of the platform were recorded. It was found that OEGJ-treated SAM mice exhibited a significantly shorter escape latency compared to the vehicle-treated mice (FIG. 7, $P<0.001$).

Ultrasound Doppler Velocity Assessment of the Cerebral Blood Flow (CBF).

The CBF of the experimental mice was studied with a 12-MHz linear probe of the Toshiba ultrasound scanner after 4 weeks OEGJ treatment. To rule out the possibility of vessel dilation effect of OEGJ, after 4 weeks OEGJ treatment, the CBF was determined 2 weeks after the OEGJ treatment. The average of 3 repeated measurements was taken as the CBF. The presence of intracranial collateral circulation was confirmed by histopathological studies. It was found that the CBF in OEGJ-treated mice was on average 15% higher than that in vehicle-treated control mice. This result indicated that OEGJ treatment induced growth of new collateral vessels in the brain of mice that reduced the peripheral resistance of arterioles or micro-vessels so that significant more blood flow to the brain was achieved, which was further confirmed by histological studies.

Measurement of Neovascularization in the SAMP10 Mouse Brain.

Histological examination revealed that the average weight of brain in OEGJ-treated mice is 14.6±4.8% heavier than that in vehicle-treated control mice (P<0.01). Brains from the SAM mice sacrificed after CBF measurement were removed, fixed in formalin and embedded in paraffin. Thin sections (5 µm) were cut from each slide and stained with H&E staining. The vascular densities were determined on the histology sections by counting the numbers of vessels within the cortex of frontal lobe and around hippocampus regions using a light microscope under a high power field (HPF) (40×). Six random and non-overlapping HPFs within the frontal lobe or hippocampus were used for counting all the vessels in each section. The number of vessels in each HPF was averaged and expressed as the number of vessels per HPF. Vascular counts were performed by two investigators in a blind fashion.

Figure 8:
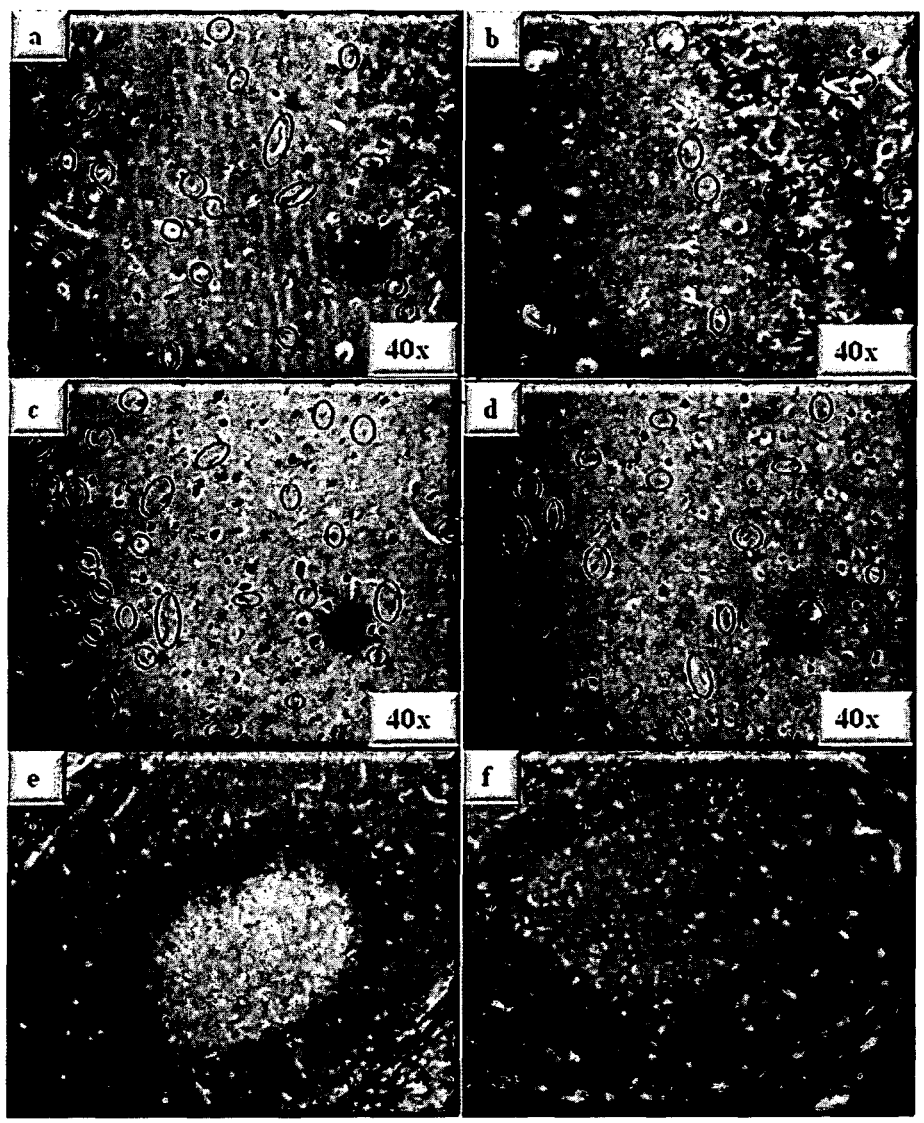
FIG. 8. Measurement of blood vessel density in regions of cortex of frontal lobe and hippocampus of SAMP10 mice. (a) A representative hippocampus region of OEGJ-treated mice showing significantly more blood vessels than that of vehicle-treated in (b) ($P<0.01$); (c) regions of cortex of frontal lobe of OEGJ-treated mice with significantly more blood vessels (circled) observed compared with that of vehicle-treated mice (d) ($P<0.05$); (e) the whole hippocampus shows relatively intact, dense and thick granule cells layers in OEGJ-treated mice; and (f) by contrast, the granule cell layers were loose and porous in vehicle-treated mice.

It was found that the numbers of vessels are about 82.3±15.6/HPF in the regions of cortex in frontal lobe and 52.0±21/HPF around the regions of hippocampus in vehicle-treated SAMP10 mice (FIG. 8). By contrast, the numbers of vessels are about 91.0±16.3/HPF in regions of cortex in frontal lobe and 72.0±15.6/HPF around the regions of hippocampus in OEGJ-treated mice (FIG. 8). The granule cell layers in hippocampus of OEGJ-treated mice showed relative intact, dense and thick. By contrast, the granule cell layers were loose and porous in vehicle-treated mice (FIG. 8).

Neuronal Regeneration.

Figure 9:
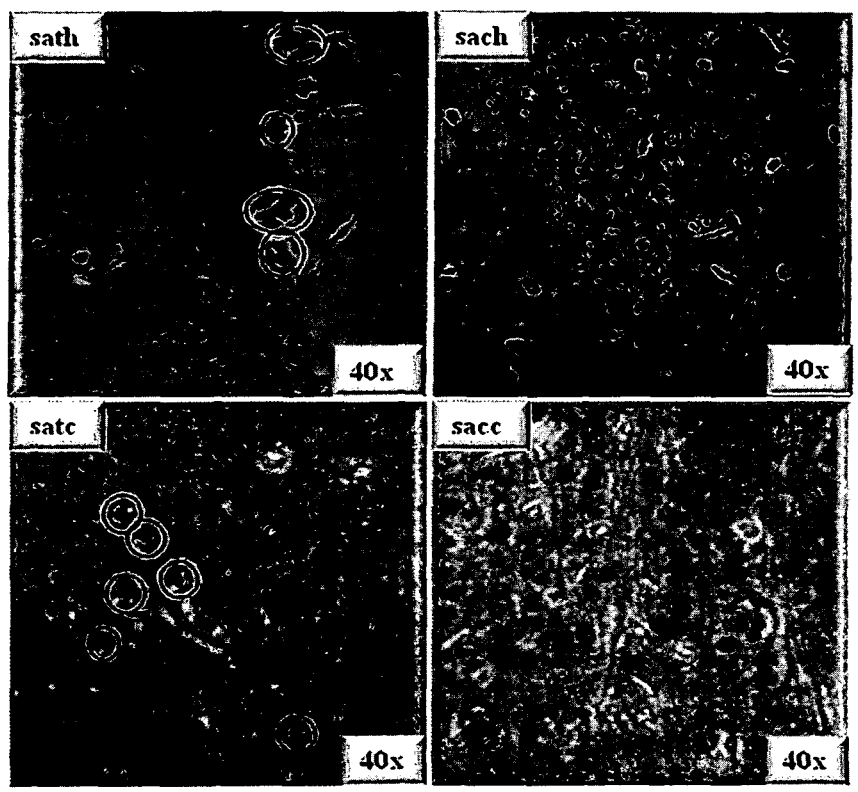
FIG. 9. OEGJ-stimulated neuronal regeneration in SAMP10 mice. (sath) Immunohistochemically stained thin section of brain from OEGJ-treated mice with Ki67 specific antibodies showing Ki67 positively stained granule neurons (circles) in hippocampus region; (sach) almost no Ki67 positively stained granule neurons found in hippocampus region of vehicle-treated mice; (satc) some Ki67 positively stained neural cells (circles) observed in cortex region of frontal lobe in OEGJ-treated mice; and (sacc) by contrast, few Ki67 positively stained neural cells found in cortex region of frontal lobe in vehicle-treated mice.

Thin sections (5 µm) were cut from each slide and immunohistochemically stained with specific antibodies against Ki67. On microscope examination of the sections, it was found that OEGJ treatment not only enhanced the growth of new blood vessels in the regions of cortex and hippocampus, but also induced neuronal regeneration in these regions (FIG. 9). By contrast, no significant growth of the new collateral vessels in the brain was identified and neither the regeneration of new neuron cells in the non-treated control brains (FIG. 9). The newly regenerated neuron-like cells were positively stained with antibodies specific to Ki67 (FIG. 9) indicating that they are newly regenerated neuronal cells.

In sum, these observations demonstrate that OEGJ not only stimulated the substantial growth of new collateral vessels in brain of SAM mice resulting in improved CBF, but also induced neuronal regeneration in cortex of frontal lobe and hippocampus regions that are responsible for learning and cognitive abilities, which may help substantially improve performance in water maze exploration tests.

OEGJ-Induced Improvement in Learning and Memory of APP Mice.

Morris water maze (1.8 M) was used in both OEGJ-treated group and vehicle-treated group to assess their spatial learning and memory capacity. No difference was detected in escape latency time to a hidden platform among both groups in water maze test before treatment. The APP mice of 6 months old were randomly divided into OEGJ-treated group (n=15) and vehicle-treated group (n=14). The mice in the OEGJ treatment group were intragastricly administered daily with an OEGJ suspension (480 mg/kg/day in water) for 30 days. The animals in vehicle treatment group were administered an equal volume of water daily. Four weeks after the OEGJ treatment, the APP mice were trained with water maze 3 times a day for 4 days. The time spent prior to finding the hidden platform, also known as escape latency, was recorded. One day after the training course, the mice were subjected to a probe trial in which the platform was removed and their memory for platform location was assessed. Typically time spent in the target quadrant (where the platform was previously located) was used to assess the strength of the memory of the mouse for the platform location. The average swim distance from the previous platform location and the number of crossings over the exact location of the platform were recorded. It was found that the vehicle-treated animals exhibited a significantly longer latency in finding the hidden platform compared to the performance in OEGJ-treated mice (FIG. 10) (P<0.01). The prolonged escape latency in the vehicle treated control mice could be significantly reduced by OEGJ (480 mg/kg/day for one month) treatment (P<0.01). The probe trial was carried out on day 5 after the day of last training trial. It was found that there were significant group effects on the time spent in the target quadrant where the platform had been located during the training trials (FIG. 10). The OEGJ treated APP mice exhibited a significantly higher number of platform crossings than the vehicle-treated mice did (FIG. 10) (P<0.01). The OEGJ-treated mice spent approximately 40% of their swimming time in the trained platform quadrant that is significantly higher than probability (25%) of chance (FIG. 10). In comparison, the mice in vehicle treated group spent about 26% of their swimming time in the trained platform quadrant, which is similar to the probability (25%) of chance and significantly shorter than that in OEGJ-treated mice (FIG. 10) (P<0.01).

Ultrasound Evaluation of the Cerebral Blood Flow (CBF).

The CBF of the APP mice was studied with a 12-MHz linear probe of the Toshiba ultrasound scanner 2 weeks after the OEGJ treatment. It was found that the CBF in OEGJ-treated APP mice was an average of 14.8% higher than that in vehicle-treated control mice indicating OEGJ treatment induced growth of new collateral vessels in brain of the APP mice that reduced the peripheral resistance of arterioles or microvessels so that more blood flow to the brain was attained.

Measurement of Neovascularization in the Brain.

Brains from the APP mice sacrificed after CBF measurement were removed and weighed. It was found that the average weight of brain in OEGJ-treated mice is approximately 15.3±3.93% heavier than that in vehicle-treated control mice (P<0.01). The brain was then fixed in formalin and embedded in paraffin. Thin sections (5 μm thick) were cut from each slide and stained with H&E staining. The vascular densities were determined on the histology sections by counting the numbers of vessels within the cortex of frontal lobe and around hippocampus regions using a light microscope under a high power field (HPF) (40×). Six random and non-overlapping HPFs within the frontal lobe or hippocampus were used for counting all the vessels in each section. The number of vessels in each HPF was averaged and expressed as the number of vessels per HPF. Vascular counts were performed by two investigators in a blind fashion.

Figure 11:
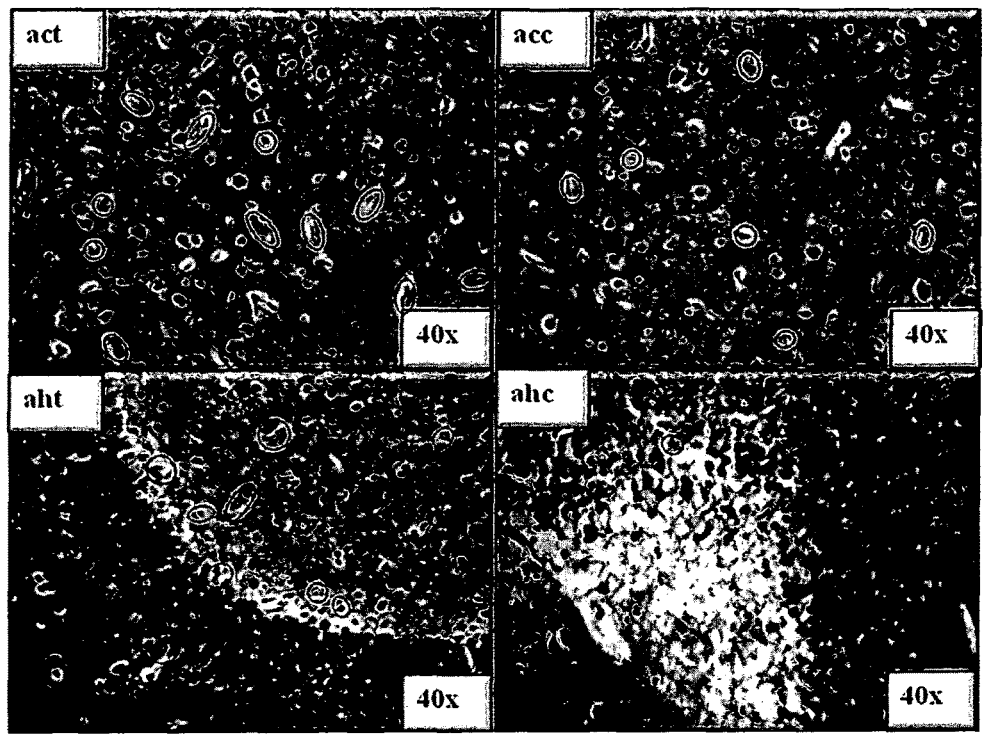
FIG. 11. Measurement of neovascularization in APP mice. (act) The representative image of cortex of frontal lobe in OEGJ-treated mice showing significantly more vessels (~78.5±19/HPF) compared with that (41.7±8/HPF) in vehicle-treated mice (acc) (circles); (aht) the representative view of hippocampus region in OEGJ-treated mice showing more vessels (79.8±23/HPF); and (ahc) by contrast, fewer vessels (39.7±8.2/HPF) were observed in the region of hippocampus of vehicle-treated control mice (circles).

It was found that the numbers of vessels are about 78.5±19/HPF in the regions of cortex in frontal lobe and 79.8±23/HPF around the regions of hippocampus in OEGJ-treated mice (FIG. 11). By contrast, the numbers of vessels are about 41.7±8/HPF in regions of cortex in frontal lobe and 39.7±8.2/HPF around the regions of hippocampus in vehicle-treated mice (FIG. 11).

Neuronal Regeneration.

Figure 12:
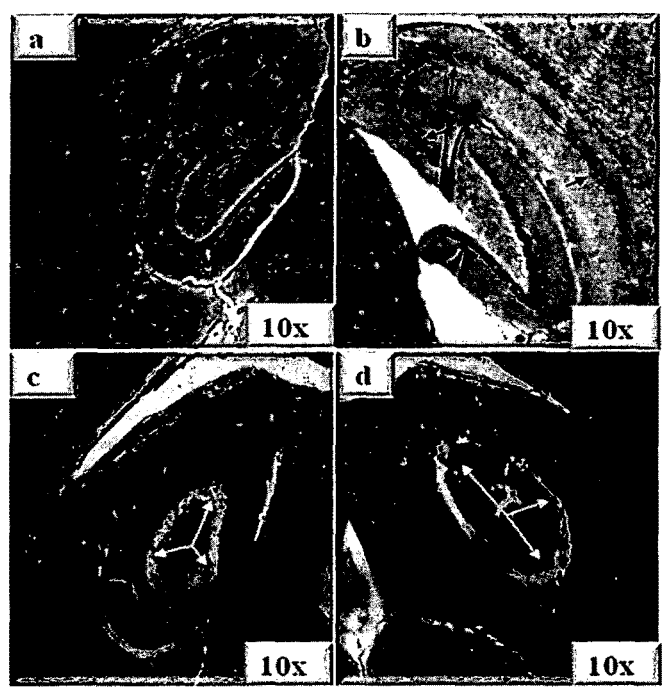
FIG. 12. Histological evaluation of hippocampus in APP mice. (a) and (b) The horizontal sections of hippocampus of both hemispheres in OEGJ-treated APP mice; (c) and (d) the horizontal section of hippocampus of both hemispheres in vehicle-treated animals. The pyramidal cell layer of all CA regions (arrowheads) of the hippocampus in vehicle-treated mice (c & d) were significantly thinned as compared to that in OEGJ-treated animals (arrowheads in a and b). Many dentate gyms (DG) granule neurons around the inner edge of DG granule cell layer (arrowheads) in vehicle-treated mice (c & d) were found distorted and died. By contrast, the DG granule cell layer in OEGJ-treated mice (a & b) remained intact; and (d) the hippocampus became shrunk and the whole DG region was partially lost in some of the vehicle-treated animals.

Microscopic study also demonstrated that the pyramidal cell layer of all CA regions of the hippocampus in vehicle-treated control APP mice showed much thinner appearance compared to that in OEGJ-treated animals (FIG. 12). Many dentate gyrus (DG) granule neurons around the inner edge of DG granule cell layer in vehicle-treated control mice were found distorted and died (FIGS. 11 & 12). By contrast, the DG granule cell layer in OEGJ-treated mice remained intact and much less DG granule neurons around the inner edge of DG granule cell layer died (FIGS. 11 & 12). Furthermore, the hippocampus in vehicle-treated APP mice became shrunk and some of the DG region was lost in some of the vehicle-treated control animals (FIG. 12). By contrast, no DG region was found lost in OEGJ-treated animals (FIG. 12).

Figure 13:
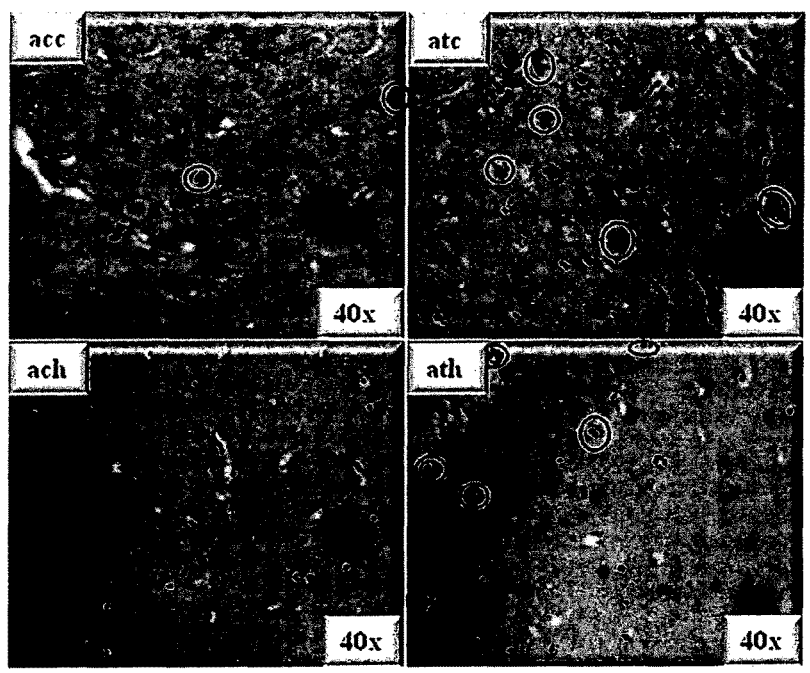
FIG. 13. Neuronal regeneration in APP mice. (acc) Immunohistochemically stained thin section of brain from vehicle-treated mice with Ki67 specific antibodies showing a few Ki67 positively stained neural cells (circles) in cortex region of frontal lobe; (atc) significantly more Ki67 positively stained neural cells (circles) found in cortex region of frontal lobe of OEGJ-treated mice; (ach) few Ki67 positively stained granule neurons (circles) observed in hippocampus region of vehicle-treated mice; and (ath) by contrast, more Ki67 positively stained granule neurons (circles) found in hippocampus region of OEGJ-treated mice.

Thin sections were immunohistochemically stained with specific antibodies against Ki67. It was shown that OEGJ treatment not only enhanced the growth of new collateral vessels in the regions of cortex and hippocampus, but also induced neuronal regeneration in cortex, hippocampus (FIG. 13). By contrast, no significant growth of the new collateral vessels in the brain was identified and neither the regeneration of new neuron cells in the non-treated control brains (FIG. 13). The newly regenerated neuron-like cells were positively stained with antibodies specific to Ki67 (FIG. 13) indicating that they are newly regenerated neuronal cells.

The aspartyl protease β-site amyloid precursor protein cleaving enzyme 1 (BACE1) initiates processing of amyloid precursor protein (APP) into amyloid β (Aβ) peptide, the major component of AD plaques. RT-PCR analysis demonstrated that BACE1 mRNA level in vehicle-treated mice was higher than that in OEGJ-treated animals (P<0.01). Aβ protein expression in vehicle-treated animals was higher than that in OEGJ-treated mice (P <0.01). BACE1 mRNA level and Aβ are reduced in the hippocampus of the APP mice by OEGJ treatment. Our histological studies also demonstrated that the amyloid plaque, visualized with Congo red staining, in OEGJ-treated SAM and APP mice was less than those in vehicle-treated animals (P<0.05). The results suggested that inhibition of BACE1 expression and Aβ generation in brain of the APP mice might underlie OEGJ's effects in improving cognitive impairment found in APP mice.

In sum, these observations imply that OEGJ not only stimulated the substantial growth of new collateral vessels in brain of SAM and APP mice resulting in significantly improved CBF, but also induced neuronal regeneration in cortex and hippocampus regions that are responsible for learning and cognitive abilities, leading to significantly improved performance in water maze exploration tests. Thus, the compositions of the present invention are useful in the treatment of AD.

Example 6—The Therapeutic Effect of OEGJ on Vascular Dementia

Vascular dementia (VD) is one of the major types of senile dementia. Recent studies suggested that chronic ischemia in the forebrain and hippocampus may be one of the major causes for VD. Therefore, we used the animal model with chronic ischemia in the forebrain by permanent bilateral common carotid artery occlusion (2VO), which is similar to human VD having learning and memory deficiency. Male Sprague-Dawley (SD) rats, weighing 300-350 g were used. The procedure for 2VO was as described previously. The rats (n=6) in test group were intragastricly administered an OEGJ suspension (480 mg/kg/day in water) for 4 weeks. The animals in vehicle-treated group (n=6) were administered an equivalent volume of water daily for an equal period.

It was found that the average weight of brains in OEGJ-treated rats was about 9.3±2.3% heavier than that in vehicle-treated rats (P<0.05). To evaluate the morphologic outcome of the 2VO model and the therapeutic effect of OEGJ, histology analysis was performed 6 weeks after 2VO. In the early stage after the permanent 2VO, the rats exerted declined movement, duck gait in hind limbs, walking ataxia, or crawl and rotation. However, a week post the operation, the experimental rats almost recovered and no apparent motor disturbance was found. Histological examination of the thin sections of forebrains demonstrated that after chronic ischemia of the brain, there were multi-cerebral ischemic lesions, progressive denaturation of the neurons in the hippocampus and cortex. The vascular densities in cortex of frontal lobe and hippocampus were measured accordingly. To quantify the average number of capillaries, 6 sections (5 μm) cut from the paraffin embedded tissue block at the interval of 50 μm respectively were analyzed. It was found that the average capillary density in OEGJ-treated brains was significantly higher than that in the vehicle-treated (P<0.005).

In conclusion, chronic cerebral ischemia induced by permanent 2VO resulted in progressive and lasting damage to the brain with the impaired learning and memory abilities, which can imitate the pathological progress of vascular dementia in humans. The compositions of the invention can restore the blood supply to the ischemic brain through collateral vessels formation and stimulate neuronal regeneration replacing the damaged neurons, and therefore, provide beneficial treatment effects on vascular dementia as confirmed by the effective therapeutic effects in dementia animal models and in humans.

Example 7—Therapeutic Effects of OEGJ on Human Patients with AD and Vascular Dementia The therapeutic effects of the compositions of the invention were tested in a clinical setting in dementia patients. Our preliminary clinical test was carried out with two male AD patients with their family member's full awareness and written consent. One patient (82 year old) started to show difficulty with many areas of mental function about one year before the treatment, including short memory loss, impaired perception, emotional behavior, trouble remembering the names and identities of himself and family members or familiar objects, getting lost on familiar routes, episode of syncope (1-2 times/month), delusional disorder, and cognitive impairment (such as calculation, abstract thinking, and judgment) (Table 1). Another patient (78 year old) started to show language problem, emotional depression and deteriorating vision about 6 months before the treatment. His symptoms also included loss of language, complete loss of vision, loss of walking ability, incontinence, inability to take care of himself, and deep depression at the time of examination (Table 2). However, after one week of the treatment with the OEGJ (oral administration, 2 grams/day), both patients reported significant improvements of the symptoms. The treatment restored their ability in remembering the names and identities of themselves and family members and significantly improved their cognitive abilities (Tables 1 & 2). Furthermore, the 82 year old patient completely recovered from his episode of syncope and delusional disorder after one-month treatment (Table 1). The 76 year old patient completely recovered from his incontinence four days after treatment. The lost of vision, language ability, communication with people, walking ability, and emotional depression were gradually restored after one-month treatment. Two months after the treatment, this 76 year old patient appeared completely normal (Table 2).

The therapeutic effects of OEGJ on human patients with vascular dementia (VD) were examined. Our preliminary clinical test was carried out with two female vascular dementia patients with their family member's full awareness and written consent. One patient (86 year old) had shown disability with many areas of mental and physical function after a severe brain attack about one and half years before treatment. She completely lost her language ability and almost all physical abilities, such as self-eating, walking, standing and even smiling. She appeared as a vegetative patient (Table 3). Another patient (82 year old) also completely lost her language and all physical ability after suffering two strokes. She appeared as a complete vegetative patient with high blood pressure and deep decubitus ulcer at the time of examination (Table 4).

However, two months treatment with the OEGJ extract (oral administration, 2 grams/day) restored the language ability, the ability to remember the names and identities of their family members and some of the physical abilities in both patients (Table 3 & 4). Furthermore, the treatment also restored some of the cognitive abilities, such as playing mahjong with a computer and making phone calls in the 86 year old patient (Table 3). The high blood pressure and difficulty in sleep were significantly improved 1 week after the treatment for the 82 year old patient (Table 4).

TABLE 1

Treatment effect of the extract on the 82 years old AD male patient

| Symptoms & Examination | Before treatment | After treatment |
|---|---|---|
| Memory Disorder | 5 | 4 |
| Perception problem | 5 | 3 |
| Confusion | 4 | 3 |
| Trouble Remembering Identities | 5 | 2 |
| Sudden collapse | 1-2 times a month | No happening |
| Delusion disorder | 4 | 1 |
| Cognitive impairment | 5 | 3 |
| Brain attack history | No | No |

1 = Not at all;
2 = A little;
3 = Moderate;
4 = Quite a bit;
5 = Extremely.

TABLE 2

Treatment effect of the extract on the 76 years old AD male patient

| Symptoms & Examination | Before treatment | After treatment |
|---|---|---|
| Loss of language ability | 4 | 1 |
| Loss of vision | 5 | 2 |
| Loss of walking ability | 4 | 2 |
| Incontinence | 5 | 1 |
| Emotional depression | 5 | 1 |
| Cognitive impairment | 4 | 2 |
| Brain attack history | No | No |

1 = Not at all;
2 = A little;
3 = Moderate;
4 = Quite a bit;
5 = Extremely.

TABLE 3

Treatment effect of the extract on the 86 years old VD patient

| Symptoms & Examination | Before treatment | After treatment |
|---|---|---|
| Loss of language ability | 5 | 3 |
| Loss of walking abilities | 5 | 4 |
| Loss of almost all other physical abilities | 4 | 3 |
| Vegetative patient | 4 | 2 |
| Cognitive impairment | 5 | 2 |
| Brain attack history | Once | No |

1 = Not at all;
2 = A little;
3 = Moderate;
4 = Quite a bit;
5 = Extremely.

TABLE 4

Treatment effect of the extract on the 82 years old VD patient

| Symptoms & Examination | Before treatment | After treatment |
|---|---|---|
| Loss of language ability | 5 | 3 |
| Loss of standing ability | 5 | 5 |
| Loss of all other physical abilities | 5 | 4 |
| Insomnia | 4 | 1 |
| Hypertension | 4 | 2 |

TABLE 4-continued

Treatment effect of the extract on the 82 years old VD patient

| Symptoms & Examination | Before treatment | After treatment |
|---|---|---|
| Vegetative patient | Yes | No |
| Brain attack history | Twice | No |

1 = Not at all;
2 = A little;
3 = Moderate;
4 = Quite a bit;
5 = Extremely.

Example 8—OEGJ Treatment Induced Improvement in Rat Model of Chronic Cerebral Ischemia Rat Chronic Cerebral Ischemia Model and Treatment Protocol.

Our preliminary studies suggested that chronic but persistent cerebral ischemia in the forebrain may be one of the major causes of neural degenerative disorders and other cognitive abilities in humans. In order to explore the beneficial usefulness of OEGJ treatment on chronic brain ischemia, we used a rat model with chronic ischemia in the forebrain, hippocampus and other lobes of the brain by permanent bilateral common carotid arteries occlusion (2VO), which resembles chronic cerebral ischemia in humans with symptoms of headache and impairment of learning and memory.

Male Sprague-Dawley (SD) rats, weighing 250-300 g were used. The study was conducted in accordance with the National Regulations of Experimental Animal Administration, and all animal experiments were approved by the Committee of Experimental Animal Administration of Zhangjiang High-tech Park. For chronic 2VO (n=11), both of the left and right common carotid arteries were exposed through a midline cervical incision under anesthesia and then they were ligated by 6-0 nylon suture, and cut by microscissors. The wound was thereafter closed with a suture. The rats (n=5) subjected to the operation but without 2VO were taken as sham-operated controls. After recovering from anesthesia, the experimental animals were allowed free access to food and water.

The rats (n=5) in the OEGJ treatment group were intragastricly administered daily with an OEGJ suspension (480 mg/kg/day in water) for 4 weeks. The animals in vehicle treatment group (n=6) were administered with an equal volume of water daily. The rats were analyzed 4 weeks after the treatment.

Doppler Ultrasound Evaluation of Brain Blood Flow.

Figure 14:
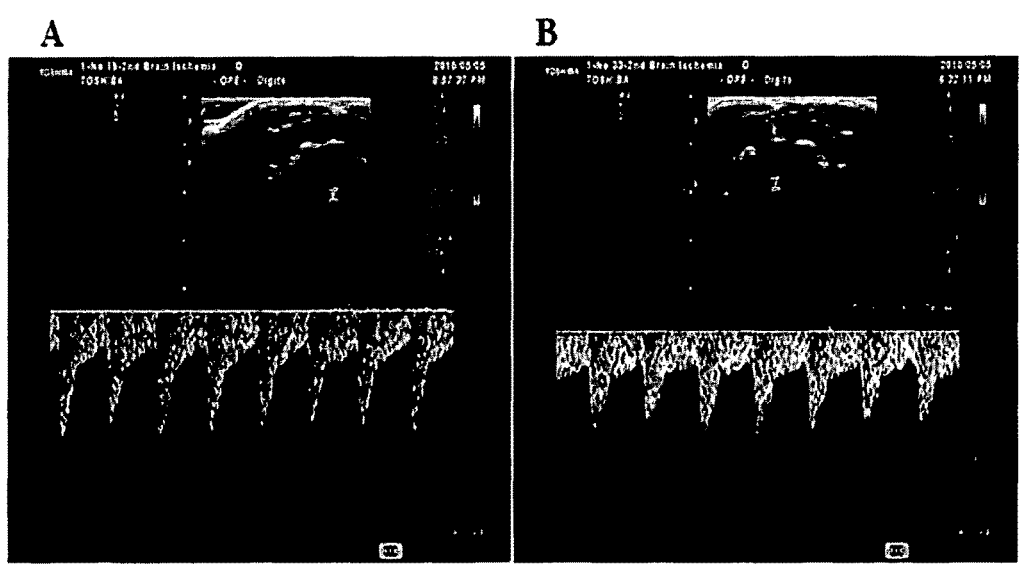
FIG. 14. Ultrasound Doppler evaluation of cerebral blood flow in chronic ischemic brain of 2VO rats. Frequency was plotted vertically and time horizontally. Each signal corresponds to one cardiac cycle. (A) Real time two dimensional image showing the basal artery (upper panel) and Doppler shift signals recorded from basal artery (lower panel) in OEGJ-treated animals; and (B) real time two dimensional image showing the basal artery (upper panel) and Doppler shift signals recorded from basal artery (lower panel) in vehicle-treated animals.

The total cerebral blood flow volume was evaluated using a Toshiba Aplio XG ultrasound with PLT-1202S linear array transducer by measuring extracranial basal artery of the experimental animals. After permanent 2VO, the blood supply to the rat brain depends dominantly on the bilateral common vertebral arteries-basal artery, which normally supplies approximately 40% of the total blood volume to the brain. Our results showed that although the blood flow volume of the basal artery in sham operated rats was around 12.4±3.5 ml/min, it reached 16.04±6.4 ml/min in vehicle-treated control due to the compensation mechanism to the 2VO, which accounts for 52% of the normal total blood volume to the brain. Interestingly, the blood flow volume of the basal artery in OEGJ-treated animals increased up to 26.8±12.80 ml/min, which is approximately 86% of the normal level of the total cerebral blood flow volume (FIG. 14).

Measurement of Neovascularization and Neuronal Regeneration in the Chronic Ischemic Brain.

When the rats were sacrificed after measurement of cerebral blood flow, it was found that the weights of brains in OEGJ-treated rats were about 8.3-11.2% heavier than those in vehicle-treated control rats (P<0.01). The paraffin thin sections (5 μm) were cut from each slide and stained with H&E staining. The vascular densities were determined on the thin sections by counting the numbers of vessels within the cortex of frontal lobe and around hippocampus regions using a light microscope under a high power field (HPF) (40×). Six sections (5 μm) cut from the paraffin embedded tissue block at the interval of 30 μm respectively were analyzed. Six random and non-overlapping HPFs within the frontal lobe or hippocampus for each section were inspected by two investigators in a blind fashion.

Figure 15:
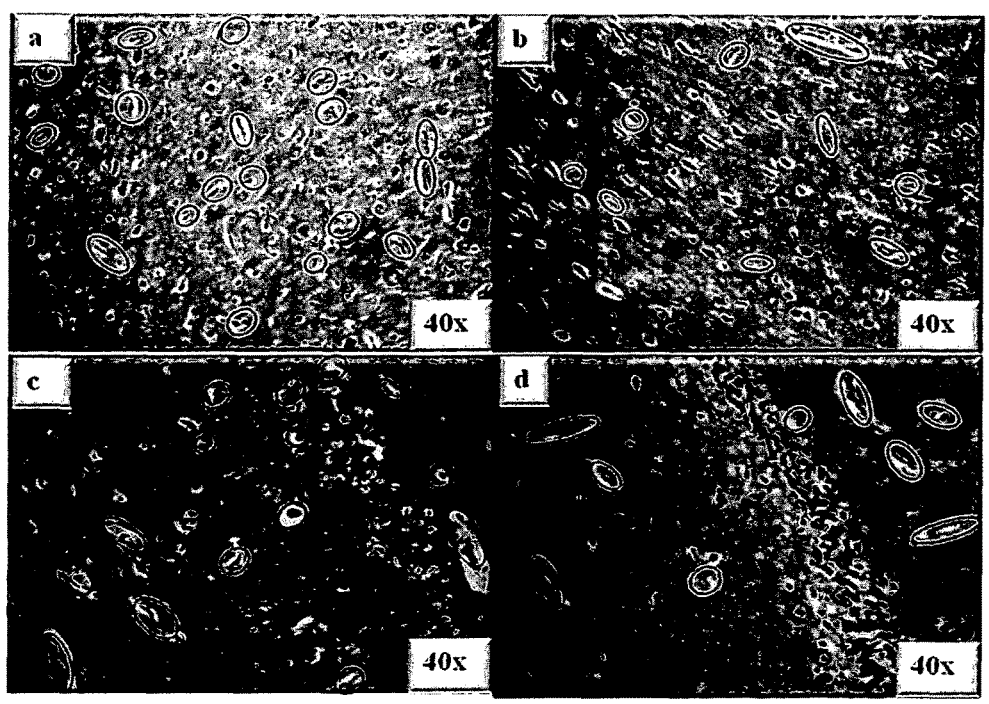
FIG. 15. OEGJ-induced neovascularization in chronic ischemic brain of 2VO rats. The horizontal sections of frontal lobes (a) and hippocampus (c) 6 weeks after 2VO and 2 weeks after OEGJ treatment. The sections of frontal lobes (b) and hippocampus (d) 6 weeks after 2VO and 2 weeks after vehicle treatment. It was found that significantly more vessels (circles) were observed in regions of cortex of frontal lobe (a) and around hippocampus (c) in OEGJ-treated animals. By contrast, fewer vessels (circles) in the similar regions (b and d) in vehicle-treated animals were observed.

It was found that the average capillary densities were about 63.3±21.1/HPF in the regions of cortex in frontal lobe (FIG. 15) and 53.6±15.2/HPF around the regions of hippocampus in OEGJ-treated rats. In comparison, the numbers of vessels were about 47.7±11.8/HPF in regions of cortex in frontal lobe (FIG. 15) and 39.5±12.3/HPF around the regions of hippocampus in vehicle-treated rats. In summary, OEGJ treatment brings about the growth of 25-35% more new vessel in ischemic brains than that of vehicle-treated (P<0.005).

Figure 16:
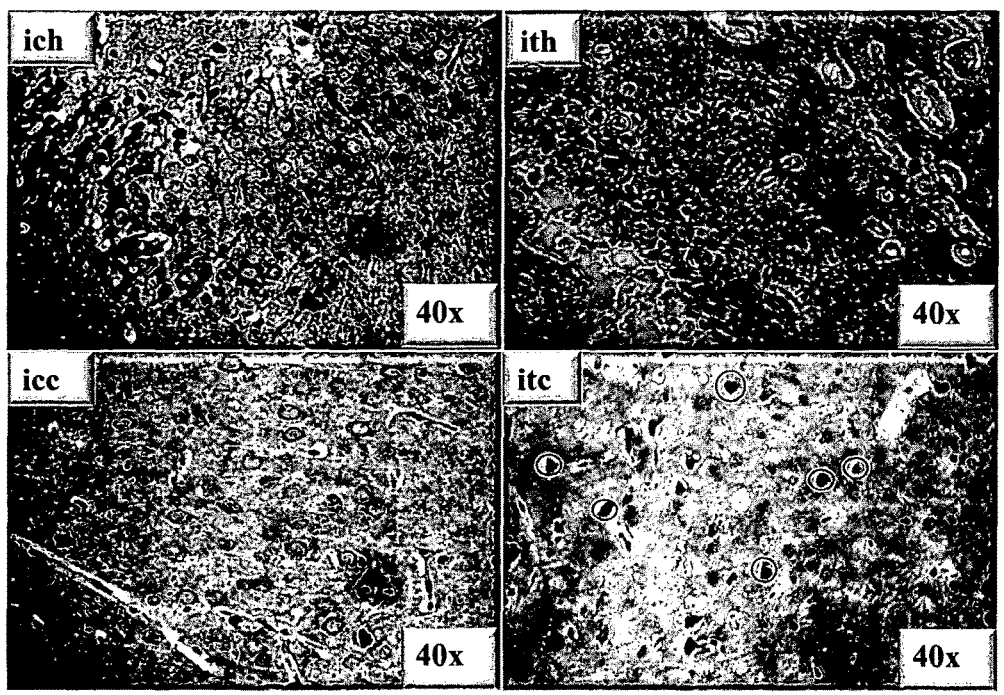
FIG. 16. OEGJ-induced neuronal regeneration in chronic ischemic brain of 2VO rats. (ich) The granule cell layer in hippocampus region of the vehicle-treated rats showing no Ki67 positively stained granule neurons; (ith) there are several Ki67 positively stained nuclei of granule neurons (circles) observed in granule cell layer of hippocampus region of the OEGJ-treated rats indicating OEGJ induced neuronal regeneration; (icc) the cortex region in frontal lobe of the vehicle-treated rats showed no Ki67 positively stained neuron-like cells; and (itc) there are circled Ki67 positively stained nuclei of neuron-like cells observed in cortex of frontal lobe of the OEGJ-treated rats indicating OEGJ induced neuronal regeneration in the cortex.

Immunohistochemistry was used to visualize the OEGJ-induced neuronal regeneration in chronic ischemic brain. The results showed that almost no Ki67 positively stained granule neurons in the granule cell layer in the hippocampus region of the vehicle-treated rats were detected (FIG. 16). In comparison, many Ki67 positively stained nuclei of granule neurons were observed in granule cell layer of the hippocampus region of the OEGJ-treated rats indicating OEGJ treatment induced neuronal regeneration. Furthermore, in the cortex region of frontal lobe in the vehicle-treated rats, there were seldom Ki67 positively stained neuron-like cells observed. However, many Ki67 positively stained nuclei of neuron-like cells were detected in cortex of frontal lobe of the OEGJ-treated rats indicating OEGJ induced neuronal regeneration in the cortex (FIG. 16).

In conclusion, chronic cerebral ischemia induced in rats by permanent 2VO resulted in progressive brain ischemia and lasting damage to the brain, which can be used to imitate the pathological progress of chronic cerebral ischemia in humans. The compositions of the present invention can restore the blood supply to the ischemic brain through collateral vessels formation, and therefore, provide beneficial treatment for chronic cerebral ischemia.

Example 9—The Therapeutic Effects of OEGJ on Chronic Cerebral Ischemia Induced by Partial Ligation of Right Carotid Artery Rat Models Male Sprague-Dawley (SD) rats, weighing 250-300 g were used. The study was conducted in accordance with the National Regulations of Experimental Animal Administration, and all animal experiments were approved by the Committee of Experimental Animal Administration of Zhangjiang High-tech Park. For creating chronic mild brain ischemia, right common carotid arteries were exposed through a midline cervical incision under anesthesia and then the artery was partially ligated (60%) by 6-0 nylon suture, and cut by microscissors. The wound was thereafter closed with a suture. The rats (n=6) subjected to the operation but without ligation were taken as sham-operated controls. After recovering from anesthesia, the experimental animals were allowed free access to food and water.

The rats (n=6) in the OEGJ treatment group were intragastricly administered daily with an OEGJ suspension (480 mg/kg/day in water) for 4 weeks. The animals in vehicle treatment group (n=6) were administered an equal volume of water daily. The rats were analyzed 4 weeks after the treatment. After partial ligation (60%) of the right carotid artery, the average blood pressure of the vehicle-treated rats was increased to approximately 140 mmHg and the total cerebral blood flow volume was around 37 ml/min. After one month of OEGJ (480 mg/kg) treatment, the average blood pressure of OEGJ-treated animals was reduced by approximately 13%, similar to the normal blood pressure level (121 mmHg), while the total cerebral blood flow volume significantly increased (50-60 ml/min) to maintain sufficient blood supply to the ischemic brain. By contrast, in the vehicle-treated animals, the cerebral blood flow was lower around 35-40 ml/min, while the blood pressure remained high around 130-150 mmHg. In summary, OEGJ treatment can rectify the chronic brain ischemia possibly by promoting the growth of new collateral vessels in the mild chronic ischemic brain.

Example 10—Effective Treatment of OEGJ in Patient with Chronic Brain Ischemia

Based on above mentioned results from the OEGJ-induced differentiation of vessel endothelial cells into capillary-like tube structures in vitro (FIG. 1) and restoration of blood supply to the ischemic brain in an animal model (FIG. 14, 15), the therapeutic effects of OEGJ was tested in a clinical setting in chronic cerebral ischemia patients with their consent on the basis of mercy treatment.

A Canadian male patient (66 years old) had mild brain ischemia for years by the time of examination. He had been frequently disturbed by a severe headache, weakness and dizziness, especially during swimming or extending his head backward. The symptoms could be relieved by oxygen therapy. He was then treated with OEGJ (3 g/daily, oral administration) for 3 weeks. It was found that all the symptoms of chronic cerebral ischemia he had suffered for years completely disappeared. The symptoms of chronic brain ischemia, such as headache, dizziness, and weakness, have not recurred in the three years following treatment. He is no longer in need of oxygen therapy since he received OEGJ treatment.

Another Malaysian female patient had chronic cerebral ischemia for years and the symptoms of the disease developed quickly and severely. She manifested the symptoms of headache, dizziness and weakness for years and suffered memory loss, poor judgment, inattentiveness, and a decrease in motor coordination. After years of treatment in hospitals, her condition deteriorated rapidly with episodes of syncope, difficulty speaking or slurred speech, auditory and visional hallucinations and personality changes. She was treated with OEGJ (2 g/daily) for two weeks initially with noticeable improvements observed, especially the improvements in speech, headache and dizziness. She continued the treatment for another 4 weeks, and most of the symptoms including speech difficulty, episodes of syncope, auditory and visional hallucinations, impaired motor coordination and headache were significantly improved. Physically, she can walk fast while keeping good body stability and balance. She appears completely normal.

Example 11—Effects of OEGJ on the Treatment of Parkinson's Disease

Based on the rather promising results from OEGJ in enhancing the differentiation of vessel endothelial cells, (FIG. 1), cerebral blood perfusion (FIG. 3, 6, 14) and neoangiogenesis (FIG. 4, 8, 11, 15), in inducing neuronal differentiation of mesenchymal stem cells in vitro (FIG. 2) and neuronal regeneration (FIG. 5, 9, 12, 16) in stroke, AD and chronic ischemic brains, OEGJ was tested in PD patients on the basis of mercy treatment. Our preliminary clinical test was carried out with two male PD patients with their family member's full awareness and written consent.

A 56 year old male from Hong Kong was diagnosed with PD three years before treatment. At early stages, he had movement disorders, such as tremor in his limbs, muscle rigidity, slowing of physical movement, postural instability and even loss of some physical movements. Prior to treatment, the symptoms of this patient developed into cognitive dysfunction and subtle language problems. He has been taking L-dopa, dopa decarboxylase inhibitors for years, which relieved the tremor but only for a short period of time. When the effects of the medicine were over, the muscles of his whole body (especially his abdomen) became so rigid that he could not stand straight and was forced to bend his back. He also complained of muscle pains, abdominal cramps, having trouble initiating movement, and stopping suddenly as he walks. Sometimes, he could not walk more than 1.5 m in an hour. He had experienced severe constipation and gastroparesis. However, after OEGJ treatment, even if there is a delay in taking his normally-prescribed medicine, which would cause difficult in initiating movement, he still could move around normally. He also feels hungry and sleepy after taking OEGJ. His constipation and gastroparesis has also been improved, defecating daily or every two days. He also complained about panic attack and short-term memory loss, and about having difficulties in going to public places, which is a condition called Parkinson's dementia, indicating the later course of the disease. After 2 weeks treatment with OEGJ (2 g/day), he now feels comfortable and confident in travelling.

Another 78 years old patient from Beijing was diagnosed with PD for more than 20 years and had tremor of his arms for more than 30 years. He has experienced similar symptoms and treatment as the 56 years old patient, but more severe. After taking OEGJ treatment, the pain in his muscle has been alleviated substantially and his abdomen is no longer cramped. One week after the OEGJ treatment (oral administration, 2 g/day), both of the patients reported significant improvements in their symptoms including muscle rigidity and gastroparesis. The treatment restored the function of their digestive tract so that the food was digested more quickly and their appetite has been restored. The treatment also relieved their constipation and abdominal pain and their cognitive abilities were gradually restored. The language ability of the 56 year old patient was also significantly improved.

While certain embodiments have been illustrated and described, it should be understood that changes and modifications can be made therein in accordance with ordinary skill in the art without departing from the technology in its broader aspects as defined in the following claims.

The present disclosure is not to be limited in terms of the particular embodiments described in this application. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, compositions or biological systems, which can, of course, vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above. Finally, as will be understood by one skilled in the art, a range includes each individual member. Thus, for example, a group having 1-3 units refers to groups having 1, 2, or 3 units. Similarly, a group having 1-5 units refers to groups having 1, 2, 3, 4, or 5 units, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

REFERENCES

Medsger, Oliver Perry (1972) Edible Wild Plants. London: Collier-Macmillan Limited Bell R D & Zlokovic B V (2009) Neurovascular mechanisms and blood-brain barrier disorder in Alzheimer's disease. *Acta Neuropathlogoy* 118:103-113.

Selkoe D J. (1991) The molecular pathology of Alzheimer's disease. Neuron 6: 487-498.

Glenner G G & Wong C W (1984) Alzheimer's disease: initial report of the purification and characterization of a novel cerebrovascular amyloid protein: *Biochem Biophys Res Commun.* 120: 885-890.

Kavirajan H & Schneider L S (2007) Efficacy and adverse effects of cholinesterase inhibitors and memantine in vascular dementia: a meta-analysis of randomised controlled trials. *Lancet Neurol.* 6:782-792.

Demaerschalk B M & Wingerchuk D M (2007) Treatment of vascular dementia and vascular cognitive impairment. *Neurologist* 13, 37-41.

Lleo A, Greenberg S M & Growdon J H (2006) Current pharmacotherapy for Alzheimer's disease. *Annu Rev Med.* 57:513-533.

de la Torre J C (2004) Is Alzheimer's disease a neurodegenerative or a vascular disorder? Data, dogma, and dialectics. *Lancet Neurol* 3: 184-190. Bell R D & Zlokovic B V (2009) Neurovascular mechanisms and blood-brain barrier disorder in Alzheimer's disease. *Acta Neuropathologica* 118: 103-113.

de la Tone J C (2006) How do heart disease and stroke become risk factors for Alzheimer's disease? *Neurol Res* 28: 637-644.

Goldsmith H S, Weilie W, Zhong J & Edgar M (2003) Omental transportation to the brain as a surgical method for treating Alzheimer's disease. *Neurol Res* 25: 625-634.

Goldsmith H S, BacciuM, Cosso M & Pau A (1990) Regional cerebral blood flow after omental transposition to the ischemic brain in man: A five-year follow-up study. *Acta Neurochir* 106: 145-152.

Goldsmith H S (2001) Role of the omentum in the treatment of Alzheimer's disease. *Neurol Res* 23: 555-564.

Takeda T, Hosokawa M & Higuchi K (1991) Senescence-accelerated mouse (SAM): a novel murine model of accelerated senescence. *Journal of the American Geriatrics Society* 39: 911-919.

Farkas E, Luiten P G M & Baric F (2007) Permanent, bilateral common carotid artery occlusion in the rat: A model for chronic cerebral hypoperfusion-related neurodegenerative diseases. *Brain Research Reviews* 54: 162-180.

Frackowiak R S J, Lenzi G L, Jones T & Heather J D (1980) Quantitative measurement of regional cerebral blood flow and oxygen metabolism in man using $^{15}O$ and positron emission tomography: theory, procedure and normal values. *Journal of Computer Assisted Tomography* 4:727-736.

Buijs P C, Krabbe-Hartkamp M J, Bakker C J, de Lange E E, Ramos L M, Breteler M M & Mali W P (1998) Effect of age on cerebral blood flow: measurement with ungated two-dimensional phase-contrast MR angiography in 250 adults. *Radiology* 209:667-74.

Spilt A, Weverling-Rijnsburger A W, Middelkoop H A, van Der Flier W M, Gussekllo J, de Craen A J, Bollen E L, Blauw G J, van Buchem M A, Westendorp R G (2005) Late-onset dementia: structural brain damage and total cerebral blood flow. *Radiology* 236: 990-995.

Farkas E & Luiten P G M (2001) Cerebral microvascular pathology in aging and Alzheimer's disease. *Prog. Neurobiol.* 64: 575-611.

Perlman J M (1997) Intrapartum hypoxic-ischemic cerebral injury and subsequent cerebral palsy: medicolegal issues. *Pediatrics* 99:851-859.

Cheng L, Chen H, Yao X, Qi G, Liu H, Lee K, Lee K, Zhang J, Chen S & Li M (2009) A Plant-derived remedy for repair of infarcted heart. *Plos One* 4: e4461.

Fakkas E, de Wilde M C, Kiliaan A J & Luiten P G (2002) Chronic cerebral hypoperfusion-related neuropathologic changes and compromised cognitive status: window of treatment. *Drugs of Today* 38: 365-376.

Roman G C (2004) Brain hypoperfusion: a critical factor in vascular dementia. *Neurological Research* 26:454-458.

Chmayssani M, Festa J R, & Marshall R S (2007) Chronic ischemia and neurocognition. *Neuroimaging Clinics of North America* 17:313-324.

What is claimed is:

1. A method for therapeutic treatment of a degenerative neuronal disease or condition in a mammalian subject, the method comprising: administering to a subject in need thereof an effective amount of an organic extract of *Geum japonicum*, wherein the extract is an ethanol extract of *Geum japonicum*, wherein the degenerative neuronal disease or condition is selected from the group consisting of: ischemic stroke, Alzheimer's disease, vascular dementia, mild cognitive impairment (MCI), chronic cerebral ischemia, and Parkinson's disease.

2. The method of claim 1, wherein the administration enhances brain blood perfusion or neuronal regeneration in a subject having an ischemic stroke compared to a control subject not administered the extract of *Geum japonicum*.

3. The method of claim 1, wherein the extract of *Geum japonicum* induces angiogenesis of an ischemic brain thereby enhancing blood perfusion.

4. The method of claim 1, wherein the extract of *Geum japonicum* is administered in an amount ranging from about 0.001 mg to about 10 g of the extract per kilogram of subject body weight per day.

5. The method of claim 1, wherein the extract of *Geum japonicum* is administered in a dosage unit form including a pharmaceutically acceptable carrier.

6. The method of claim 1, wherein the extract of *Geum japonicum* stimulates neuronal regeneration.

7. The method of claim 1, wherein the extract of *Geum japonicum* reduces the size of the brain ischemic infarcted area compared to a control subject not administered the extract of *Geum japonicum*.

8. The method of claim 1, wherein the extract of *Geum japonicum* is administered orally.

9. The method of claim 1, wherein the extract of *Geum japonicum* is administered by subcutaneous injection, intramuscular injection, or intravenous infusion.

10. The method of claim 1, wherein the subject is a human.

* * * * *